(12) United States Patent
Jais et al.

(10) Patent No.: US 7,412,273 B2
(45) Date of Patent: Aug. 12, 2008

(54) SOFT LINEAR MAPPING CATHETER WITH STABILIZING TIP

(75) Inventors: Pierre Jais, Pessac-Bordeaux (FR); Irma P. Hill, La Verne, CA (US); James K. Lee, West Covina, CA (US); Robert A. Mest, Long Beach, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 196 days.

(21) Appl. No.: 10/990,146

(22) Filed: Nov. 15, 2004

(65) Prior Publication Data

US 2006/0106295 A1 May 18, 2006

(51) Int. Cl.
*A61B 5/04* (2006.01)

(52) U.S. Cl. .................................. 600/374; 600/381
(58) Field of Classification Search ................. 600/374, 600/381
See application file for complete search history.

(56) References Cited

U.S. PATENT DOCUMENTS

| 5,487,385 | A | 1/1996 | Avitall |
| 5,617,854 | A | 4/1997 | Munsif |
| 7,142,903 | B2 * | 11/2006 | Rodriguez et al. .......... 600/374 |
| 2003/0130572 | A1 | 7/2003 | Phan et al. |

FOREIGN PATENT DOCUMENTS

WO WO 94/16618 8/1994

OTHER PUBLICATIONS

International Search Report dated Mar. 29, 2006 for International Application No. PCT/US2005/041284.
Written Opinion dated Mar. 29, 2006 for International Application No.PCT/US2005/041284.

* cited by examiner

*Primary Examiner*—Lee S Cohen
(74) *Attorney, Agent, or Firm*—Christie, Parker & Hale, LLP

(57) ABSTRACT

A catheter adapted for mapping near a tubular region of a heart, has an elongated tubular catheter body having proximal and distal ends, an intermediate section distal of the catheter body, and a mapping assembly at the distal end of the intermediate section. The electrode-carrying mapping assembly has a generally circular main segment with a support member having shape-memory, and a generally linear proximal segment which has greater flexibility than either the intermediate section or the generally circular main segment. The generally circular main segment is adapted to releasably anchor itself in the tubular region and to map circumferentially around the tubular region and the generally linear segment is adapted to contact generally along its length heart wall tissue near an ostium of the tubular region. In another embodiment of the present invention, the mapping assembly extends from the distal end of the catheter body, where the generally linear proximal segment of the mapping assembly has greater flexibility than either the catheter body or the generally circular main segment.

37 Claims, 18 Drawing Sheets

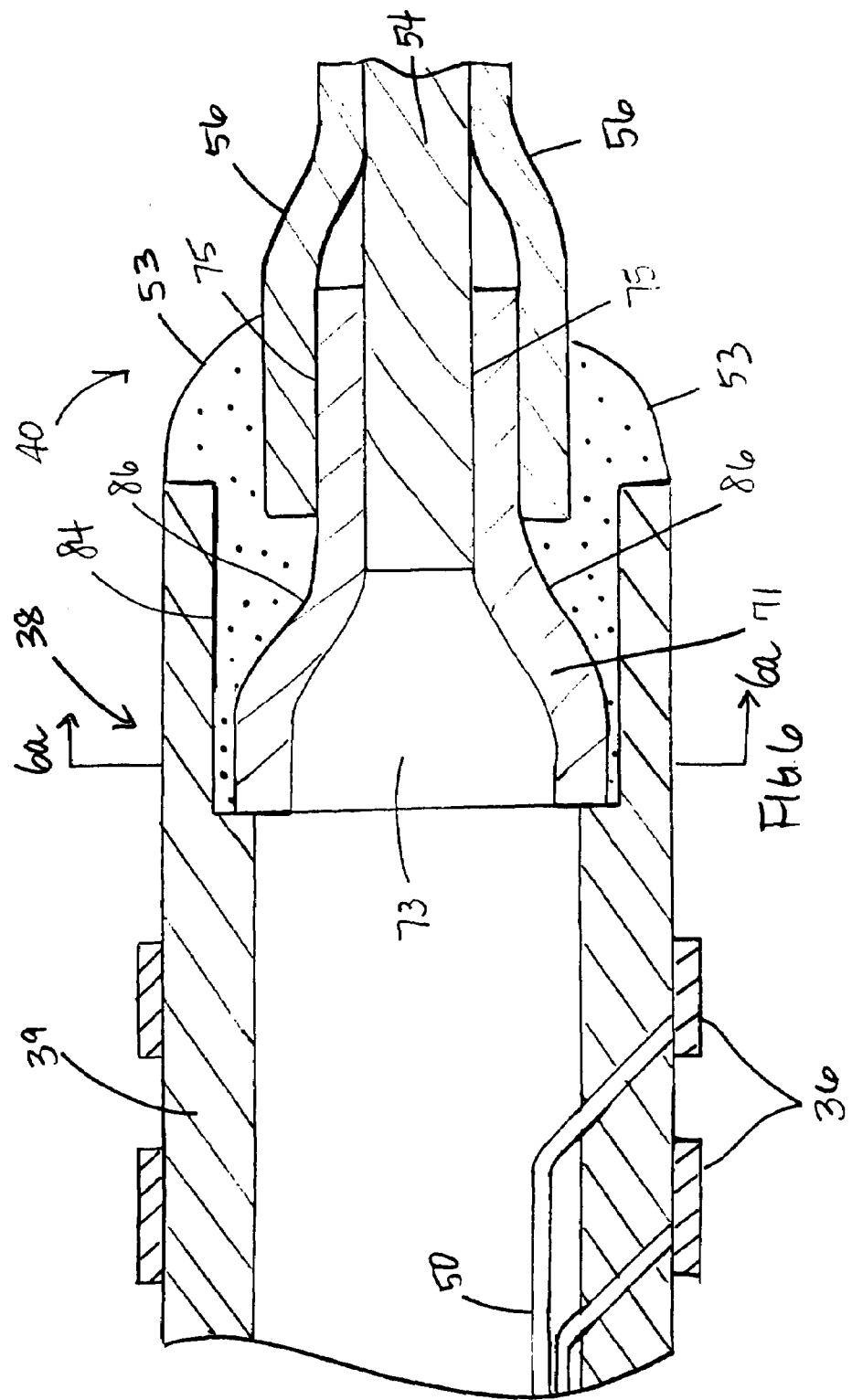

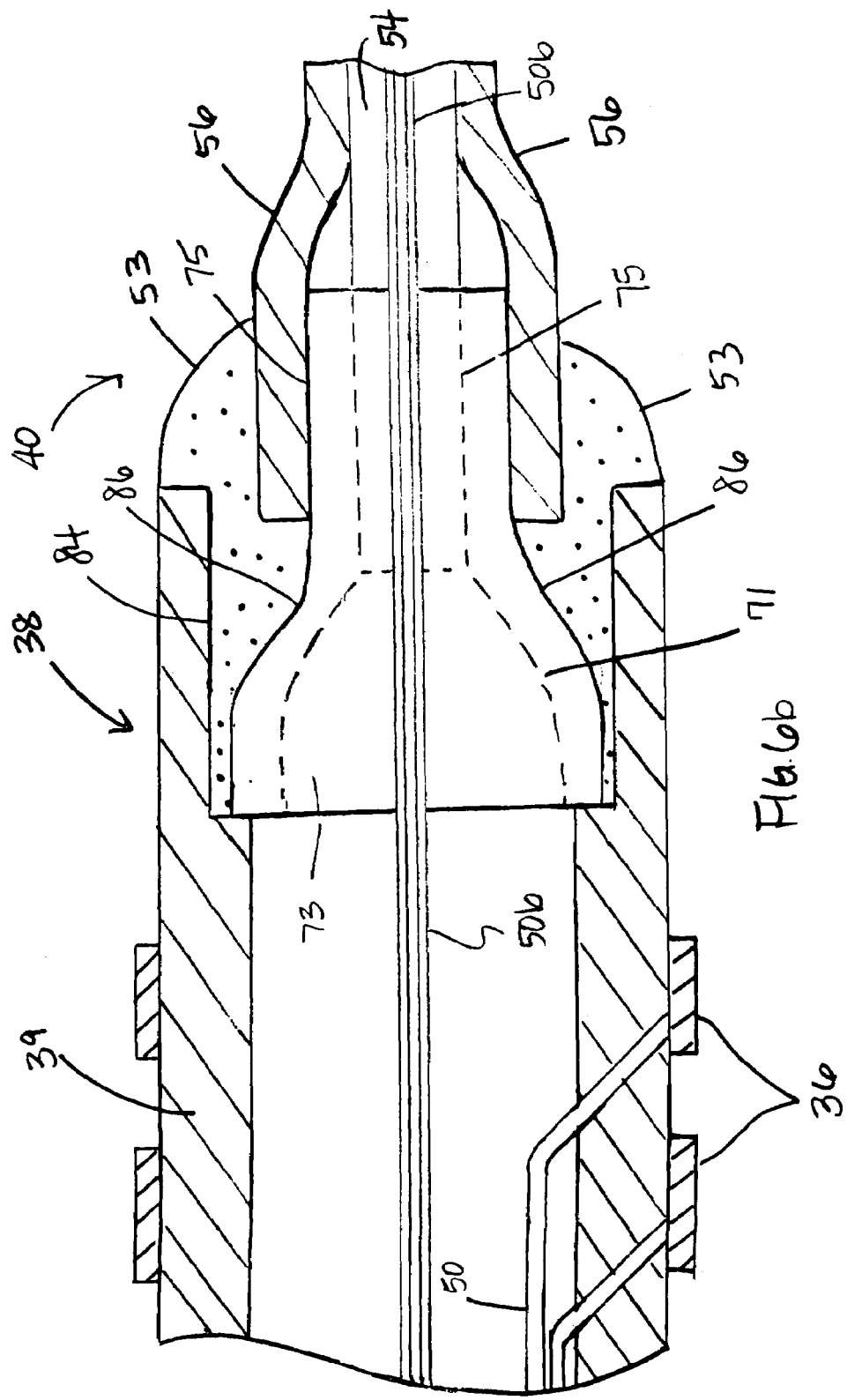

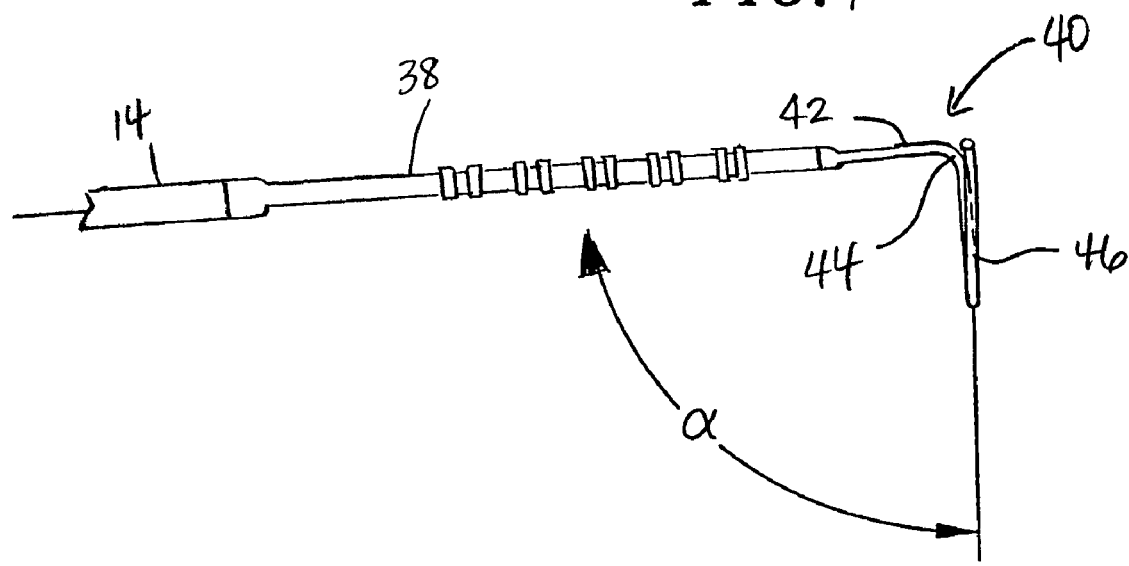
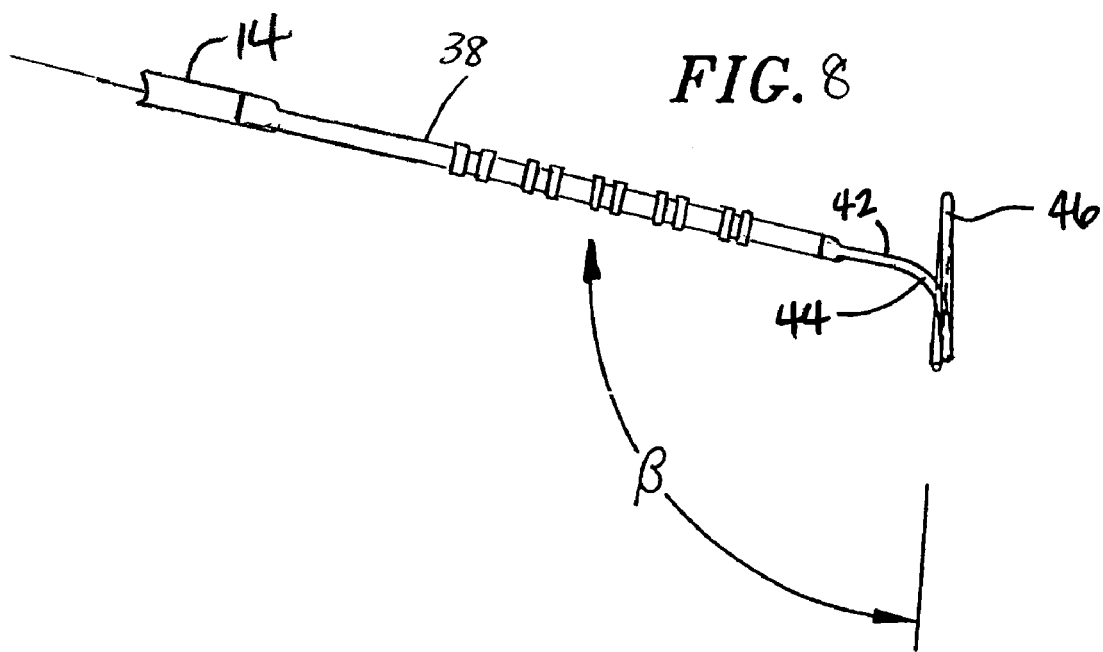

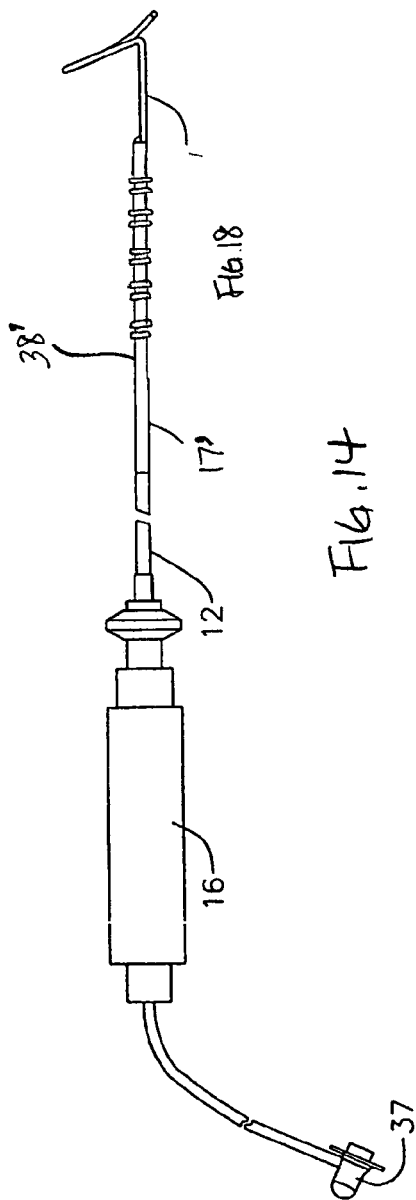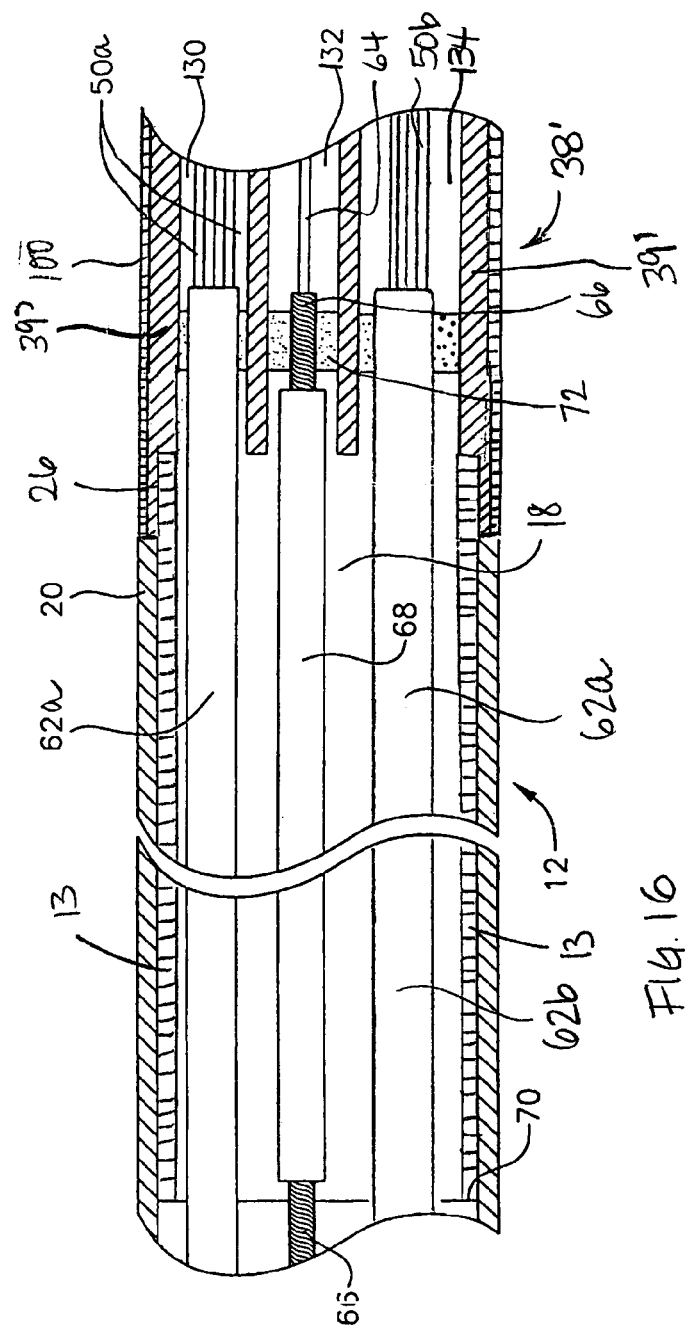

SOFT LINEAR MAPPING CATHETER WITH STABILIZING TIP

FIELD OF INVENTION

The present invention relates to an improved mapping catheter that is particularly useful for mapping electrical activity in a wall region of or near the heart.

BACKGROUND OF INVENTION

Atrial fibrillation is a common sustained cardiac arrhythmia and a major cause of stroke. Atrial fibrillation results in a fast and irregular cardiac rhythm which often leads to palpitations and a deterioration of cardiac function with cardiac output decreasing by an average of 30%. There is also an increased incidence of intra cardiac thrombosis (blood clotting) which can potentially lead to embolic events such as strokes. Consequently, 20 to 35% of cerebrovascular accidents (CVAs) are related to paroxysmal or chronic atrial fibrillation.

This condition is perpetuated by reentrant wavelets propagating in an abnormal atrial-tissue substrate. Various approaches have been developed to interrupt wavelets, including surgical or catheter-mediated atriotomy. Atrial fibrillations can also be treated by pulmonary vein isolation which proves to be insufficient in 30 to 50% of paroxysmal atrial fibrillation patients and 90% of permanent atrial fibrillation. In such cases, it may be necessary to ablate and perform linear lesions in addition to pulmonary vein isolation, in the right and left atriums. These linear lesions have been done using RF ablation catheters for about a decade. Each lesion should ideally be transmural and continued with adjacent lesions so as to obtain a final linear lesion blocking electrical activity between two natural areas of block. The most common locations of these lines are the mitral isthmus in the left atrium, with a lesion extending from the mitral annulus to the left inferior pulmonary vein. Other possible locations include the roof of the left atrium, with a lesion connecting the ostium of the superior right pulmonary vein to the left superior vein. However, because conventional catheters generally treat tissue in a localized manner, numerous repeated applications of the catheter are typically needed to form a linear lesion. Thus, while the formation of linear lesions is possible, it can be a time-consuming, labor-intensive procedure.

Prior to treating the condition, one has to first determine the location of the wavelets. Various techniques have been proposed for making such a determination. None of the proposed techniques, however, provide sufficient assistance in guiding the formation of the linear lesion or easing the linear line assessment process, particularly for regions of the mistral isthmus and the left atrium roof.

SUMMARY OF THE INVENTION

A catheter adapted for mapping near a tubular region of a heart, has an elongated tubular catheter body having proximal and distal ends, an intermediate section distal of the catheter body, and a mapping assembly at the distal end of the intermediate section. The electrode-carrying mapping assembly has a generally circular main segment with a support member having shape-memory, and a generally linear proximal segment which has greater flexibility than either the intermediate section or the generally circular main segment. In accordance with the present invention, the generally circular main segment is adapted to releasably anchor itself in the tubular region and to map circumferentially around the tubular region and the generally linear segment is adapted to contact generally along its length heart wall tissue near an ostium of the tubular region. Advantageously, the mapping assembly is adapted to conduct mapping of said wall tissue along a linear pattern extending radially from the ostium. Moreover, the mapping assembly is adapted to be rotated about the ostium to perform mapping of said wall tissue along different radially-extending linear patterns about the ostium. To that end, the generally linear segment has a proximal portion that is generally devoid of electrodes and the catheter includes a control handle to deflect the catheter along the intermediate section.

In another embodiment of the present invention, a catheter adapted for mapping near a tubular region of a heart, has an elongated tubular catheter body having proximal and distal ends and a mapping assembly at the distal end of the catheter body. The electrode-carrying mapping assembly has a generally circular main segment with a support member having shape-memory, and a generally linear proximal segment which has greater flexibility than either of the catheter body and the generally circular main segment. In accordance with the present invention, the generally circular main segment is adapted to releasably anchor itself in the tubular region and to map circumferentially around the tubular region and the generally linear segment is adapted to contact generally along its length heart wall tissue near an ostium of the tubular region. Advantageously, the mapping assembly is adapted to conduct mapping of said wall tissue along a linear pattern extending radially from the ostium. Moreover, the mapping assembly is adapted to be rotated about the ostium to perform mapping of said wall tissue along different radially-extending linear patterns about the ostium. To that end, the generally linear segment has a proximal portion that is generally devoid of electrodes and the catheter includes a control handle to deflect the catheter along the generally linear segment of the mapping assembly.

In another embodiment, electrodes are carried on both the generally linear segment and the generally circular segment. In a more detailed embodiment, the generally linear segment has a length of about 30 mm and the generally circular main segment has an outer diameter of about 25 mm. Moreover, both the generally linear segment and the generally circular main segment may each carry at least five ring electrode pairs.

The present invention also includes a method for mapping electrical activity of wall tissue near a tubular region of or near the heart, the method using a catheter in accordance with the present invention. In one embodiment, the method includes inserting the generally circular segment of a catheter in accordance with the present invention into a tubular region of or near the heart, releasably anchoring the generally circular segment in the tubular region near its ostium, contacting the generally linear segment of the catheter generally along its length with wall tissue near the ostium, and mapping the electrical activity of the wall tissue along a linear pattern extending radially from the ostium. The method may also include rotating the mapping assembly about the ostium and mapping the electrical activity of the wall tissue along a different linear pattern extending radially from the ostium. The tubular region is selected from the group consisting of pulmonary veins, the coronary sinus, the superior vena cava, and the inferior vena cava.

BRIEF DESCRIPTION OF THE DRAWINGS

These and other features and advantages of the present invention will be better understood by reference to the following detailed description when considered in conjunction with the accompanying drawings wherein:

FIG. 6 is a side cross sectional view of an embodiment of the junction between the proximal region and the distal region of the mapping assembly.

FIG. 6b is a side cross sectional view of an embodiment of the junction between the proximal region and the distal region of the mapping assembly, having lead wires for electrodes on the distal region.

FIG. 7 is a side view of an embodiment of the mapping assembly according to the present invention in a clockwise formation.

FIG. 8 is a side view of the mapping assembly of FIG. 7 in a counterclockwise formation rotated 90 degrees.

FIG. 14 is a side view of an alternative embodiment of the catheter of the present invention.

FIG. 15a is a cross sectional view taken along line 15A-15A in FIG. 15.

FIG. 17a is a cross sectional view taken along lines 17a-17a in FIG. 17.

DETAILED DESCRIPTION OF THE INVENTION

Figure 1:
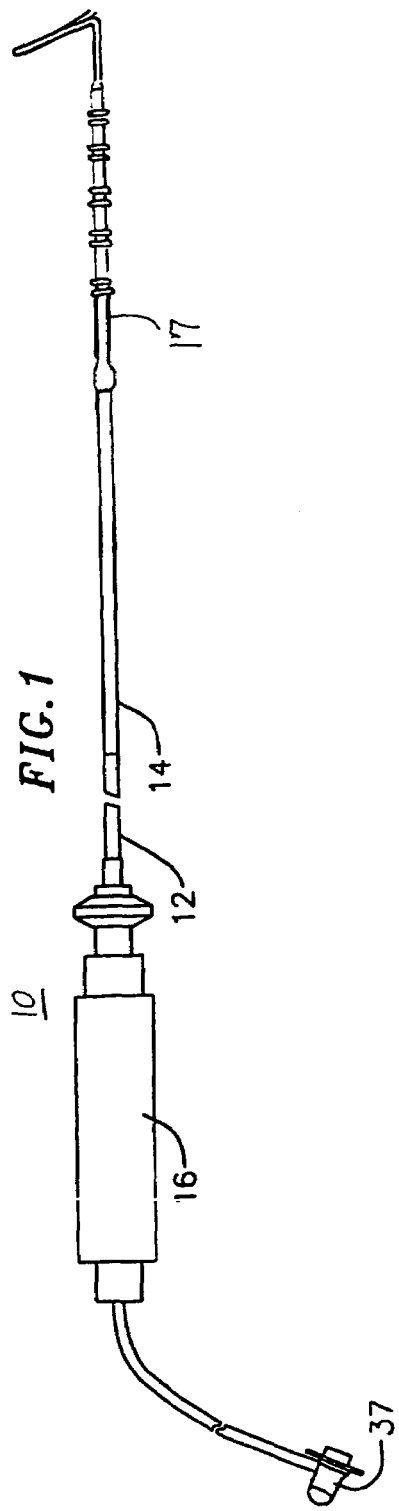
FIG. 1 is a side view of an embodiment of the catheter of the present invention.

In a disclosed embodiment of the invention, there is provided a catheter 10 having a mapping assembly at its distal end. As shown in FIG. 1, the catheter comprises an elongated catheter body 12 having proximal and distal ends, an intermediate section 14 at the distal end of the catheter body, a control handle 16 at the proximal end of the catheter body, and a mapping assembly 17 mounted at the distal end of the catheter to the intermediate section 14.

Figure 2:
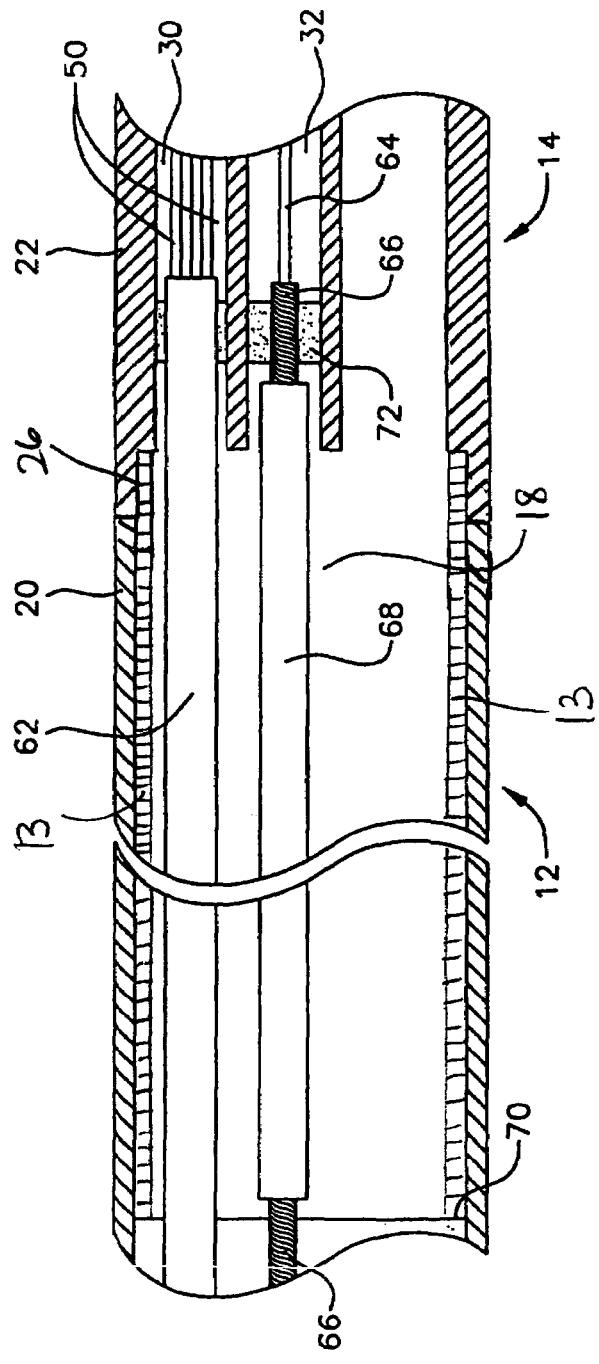
FIG. 2 is a side cross sectional view of the catheter body of FIG. 1, including the junction between the catheter body and the intermediate section.

With reference to FIG. 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate a puller wire, lead wires, and any other desired wires, cables or tubings. If desired, the inner surface of the outer wall 20 is lined with a stiffening tube (not shown) to provide improved torsional stability. A disclosed embodiment, the catheter has an outer wall 20 with an outer diameter of from about 0.090 inch to about 0.94 inch and an inner diameter of from about 0.061 inch to about 0.065 inch.

With further reference to FIG. 2, the intermediate section 14 comprises a short section of tubing 22 having three lumens. The first lumen 30 electrode carries lead wires 50 and the second lumen 32 carries a puller wire 64. There may also be third lumen 34. The tubing 22 is made of a suitable non-toxic material that is preferably more flexible than the catheter body 12. A suitable material for the tubing 22 is braided polyurethane, i.e., polyurethane with an embedded mesh of braided stainless steel or the like. The size of each lumen is not critical, but is sufficient to house the lead wires or the puller wire.

The useful length of the catheter, i.e., that portion that can be inserted into the body excluding the mapping assembly 17, can vary as desired. In one embodiment, the useful length ranges from about 110 cm to about 120 cm. The length of the intermediate section 14 is a relatively small portion of the useful length, and preferably ranges from about 3.5 cm to about 10 cm, more preferably about 4 cm to about 8 cm, and still more preferably about 6.5 cm.

A preferred means for attaching the catheter body 12 to the intermediate section 14 is illustrated in FIG. 2. The proximal end of the intermediate section 14 comprises an outer circumferential notch 26 that receives the inner surface of the outer wall 20 of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

Figure 3:
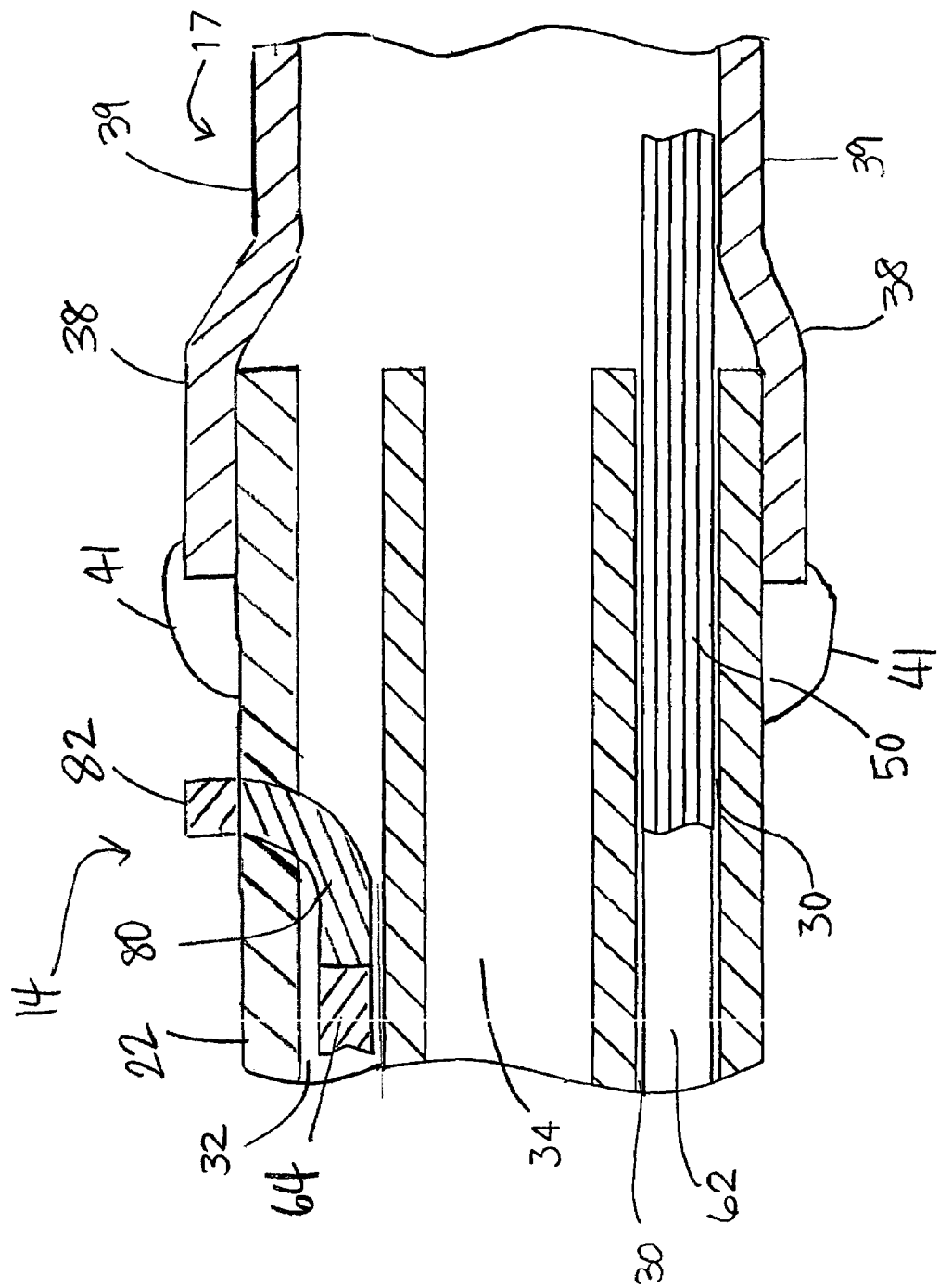
FIG. 3 is a side cross sectional view of the catheter body of FIG. 1, including the junction between the intermediate section and the mapping assembly.

Within the intermediate section 14, the puller wire 64 extends into the second lumen 32. Preferably the puller wire 64 is anchored at its distal end to the distal end of the intermediate section 14, as shown in FIG. 3. Specifically, a T-shaped anchor is formed, which comprises a short piece of tubular stainless steel 80, e.g., hypodermic stock, which is fitted over the distal end of the puller wire 64 and crimped to fixedly secure it to the puller wire. The distal end of the tubular stainless steel 80 is fixedly attached, e.g., by welding, to a cross-piece 82 formed of stainless steel ribbon or the like. The cross-piece 82 extends through a hole formed in the outer wall and because the cross-piece 82 is larger than the hole and, therefore, cannot be pulled through the hole, the cross-piece 82 anchors the distal end of the puller wire 64 to the distal end of the intermediate section 14. Within the second lumen 32 of the intermediate section 14, the puller wire 64 extends through a plastic, preferably Teflon™, puller wire sheath (not shown), which prevents the puller wire 64 from cutting into the wall of the intermediate section 14 when the intermediate section is deflected. It is understood that the puller wire 64 enables the catheter to deflect generally along the length of the intermediate section 14.

Longitudinal movement of the puller wire 64 relative to the catheter body 12, which results in deflection of the intermediate section 14 and generally the mapping assembly 17, is accomplished by suitable manipulation of the control handle 16. Examples of suitable control handles for use in the present invention are disclosed, for example, in U.S. Pat. Nos. Re 34,502 and 5,897,529, the entire disclosures of which are incorporated herein by reference.

Figure 4:
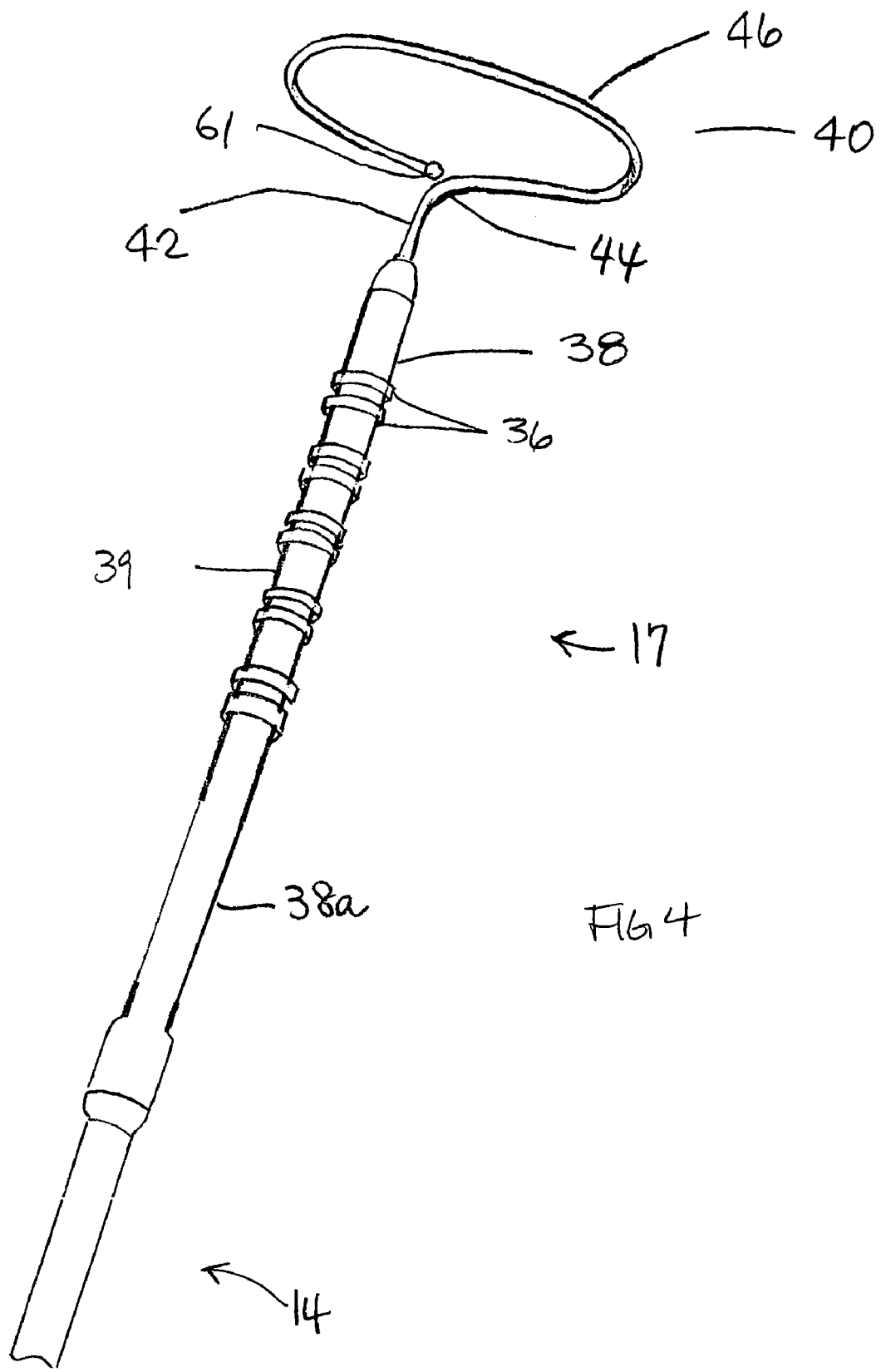
FIG. 4 is a schematic perspective view of an embodiment of the mapping assembly according to the present invention.
Figure 5:
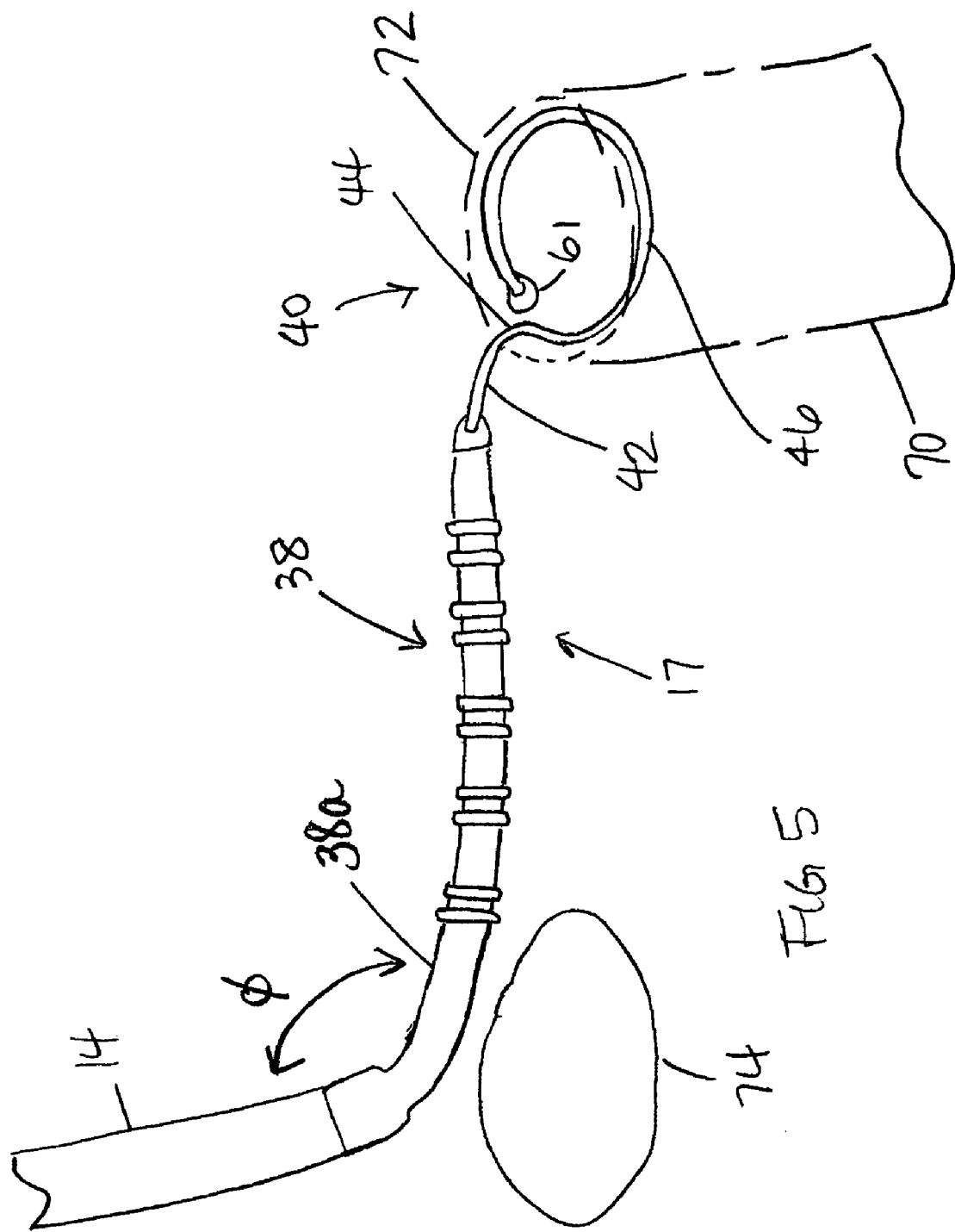
FIG. 5 is a schematic perspective view of the mapping assembly of FIG. 4 with its distal portion releasably anchored in a tubular region and its proximal portion generally lying against tissue surrounding the tubular region.

At the distal end of the intermediate section 14 is a mapping assembly 17, as shown in FIGS. 4 and 5. The mapping assembly comprises a more flexible, generally straight proximal region 38 and a less flexible but pre-shaped distal region 40 having a straight proximal segment 42, a transitional segment 44 and a generally circular main segment 46.

The proximal region 38 is mounted on the distal end of the intermediate section 14, as described in more detail below, so that its axis is generally parallel to the axis of the intermediate section, and preferably has an exposed length, e.g., not contained within the intermediate section 14, ranging from about 20 mm to about 70 mm, more preferably about 25 mm to about 50 mm, still more preferably about 42 mm, but can vary as desired.

As illustrated in FIGS. 3 and 6, the proximal region 38 comprises a tubing 39 which can be made of any suitable material that is flexible and biocompatible and preferably plastic, such as polyurethane or PEBAX. The tubing 39 may have any cross-sectional shape and may have a single lumen or multiple lumens and is generally free of any interior support members although its lumen is occupied by lead wires 50 or other electrical connections for electrodes or any other electrical or electromagnetic elements that may be mounted on the mapping assembly 17. A preferred means for attaching the tubing 39 to the intermediate section 14 is illustrated in FIG. 3. The proximal end of the tubing 39 extends over and overlaps with the distal end of the tubing 22. Glue or the like is applied between the contacting inner surface of the tubing 39 and outer surface of the tubing 22. Additional glue may be applied immediately proximal of the proximal end of the section 38 to form a seal 41.

As shown in FIGS. 4 and 5, a series of paired ring electrodes 36 are mounted on the tubing 39 of the proximal region 38. The ring electrodes 36 can be made of any suitable solid conductive material, such as platinum or gold, preferably a combination of platinum and iridium, and mounted onto the tubing 39 with glue or the like. Alternatively, the ring electrodes can be formed by coating the tubing 39 with an electrically conducting material, like platinum, gold and/or iridium. The coating can be applied using sputtering, ion beam deposition or an equivalent technique.

In a preferred embodiment with reference to FIG. 6, each ring electrode 36 is mounted by first forming a hole in the tubing 39. An electrode lead wire 50 is fed through the hole, and the ring electrode 36 is welded in place over the lead wire and tubing 39. The lead wires 50 extend through the tube 39. The proximal end of each lead wire 50 is electrically connected to a suitable connector 37 (FIG. 1), which is connected to a source of RF energy (not shown).

The number of the ring electrodes 36 on the assembly 17 can vary as desired. Preferably, the number of ring electrodes ranges from about six to about twenty, preferably from about eight to about twelve. In a disclosed embodiment, the assembly carries ten ring electrodes forming five pairs. The pairs of ring electrodes 36 are preferably approximately evenly spaced along the proximal region 38, as best shown in FIG. 4. In a disclosed embodiment, a distance of approximately 5 mm is provided between each pair of the ring electrodes 36, with each electrode within a pair separated by a distance of about 1 mm. Advantageously, the proximal region 38 includes a proximal segment 38a which is generally devoid of electrodes such that the mapping assembly 17 can generally lie against wall tissue, as shown in FIG. 5. In particular, the proximal segment 38a enables the distal end of the intermediate section 14 and the proximal end of the mapping assembly 17 (e.g., the proximal segment 38a) to define an angle phi therebetween ranging between about 45 degrees and about 315 degrees. The proximal segment 38a may have a length ranging between about 0.5 inch and about 2.0 inches, and more preferably about 1.0 inch.

As for the distal region 40 of the assembly 17, the straight segment 42 is mounted on the distal end of the proximal region 38, as described in more detail below, so that its axis is generally parallel to the axis of the proximal region 38 and preferably has an exposed, length, e.g., not contained within the proximal region 38, ranging from about 10-20, more preferably about 15 mm, but can vary as desired.

The generally circular main segment 46 is generally traverse to the catheter body 12 and is preferably generally perpendicular to the catheter body 12. The generally circular main segment need not form a flat circle, but can be very slightly helical, as shown in FIGS. 4, 7 and 8. The main segment 46 has an outer diameter preferably ranging to about 10 mm to about 35 mm, more preferably about 15 mm to about 30 mm, still more preferably about 25 mm. The transition segment 44 between the segments 42 and 46 is slightly curved and formed such that, when viewed from the side with the segment 42 at the top of the circular main segment 46 as shown in FIG. 7, the proximal segment 42 (along with the proximal region 38) forms an angle .alpha. with the circular main segment 46 ranging from about 75.degree. to about 95.degree., preferably from about 83.degree. to about 93.degree., more preferably about 87.degree. The main region segment 46 can curve in a clockwise direction, as shown in FIG. 7 or a counterclockwise direction, as shown in FIG. 8. When the assembly 17 is turned 90.degree., as shown in FIG. 8, so that the transition segment 44 is near the center of the main segment 46, the proximal segment 42 (along with the proximal region 38) forms an angle .beta. with the main circular segment 46 ranging from about 90.degree. to about 135.degree., preferably from about 100.degree. to about 110.degree., more preferably about 105.degree.

As illustrated in FIG. 6, the distal region 40 of the mapping assembly 17 is formed from a support member 54 covered by a non-conductive covering 56. The support member 54 is made of a material having shape-memory, i.e., that can be straightened or bent out of its original shape upon exertion of a force and is capable of substantially returning to its original shape upon removal of the force. A suitable material for the support member 54 is a nickel/titanium alloy. Such alloys typically comprise about 55% nickel and 45% titanium, but may comprise from about 54% to about 57% nickel with the balance being titanium. A preferred nickel/titanium alloy is nitinol, which has excellent shape memory, together with ductility, strength, corrosion resistance, electrical resistivity and temperature stability. The non-conductive covering 56 can be made of any suitable material, and is preferably made of a biocompatible plastic such as polyurethane or PEBAX.

Figure 6A:
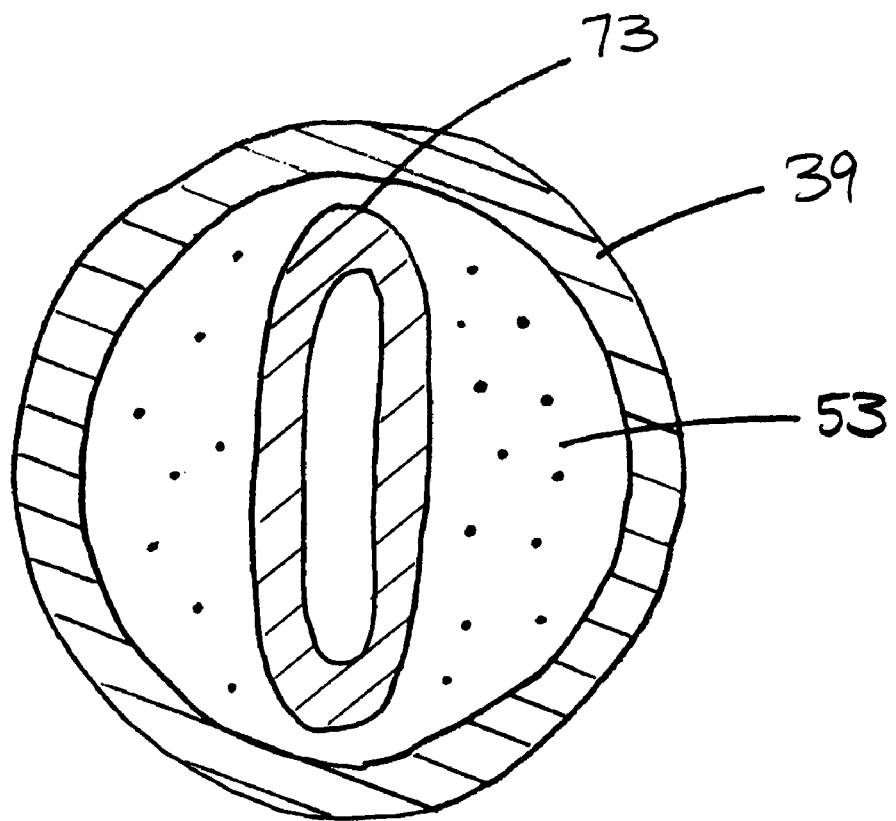
FIG. 6a is a cross sectional view taken along 6A-6A in FIG. 6.

A means for attaching the distal region 40 to the proximal region 38 is illustrated in FIG. 6. At the proximal end of the distal region 40, a stainless steel tubing 71 is welded onto the distal end of the support member 54 at their respective contacting surface 75. A proximal end of the tubing 71 is flattened or otherwise shaped to form a spade 73 with an elongated cross-section (FIG. 6A) which anchors the proximal end of the distal region 40 in the distal end of the proximal region 38. In particular, the spade 73 sit within a cored-out distal end of the tubing 39 forming a notch 84. Glue or the like is applied to the distal end of the tubing 39 to form a plug 53 sealing the region of attachment. As such, the elongated cross-section of the spade 73 anchors the distal region 40 against rotational movement about the axis of the support member 54 relative to the proximal region 38. Moreover, a base 86 of the spade 73 anchors the distal region 40 against distal movement relative to the proximal region 38.

The proximal end of the support member 54 and the non-conductive covering 56 terminate a short distance within the lumen of the tubing 39 of the proximal section 38, approximately about 5 mm, so as not to adversely affect the flexibility of the proximal section 38.

Because the proximal region 38 is generally without any internal structure other than lead wires 50 from the electrodes or perhaps a second puller wire for changing the diameter of the circular segment 46, the proximal region 38 is more flexible than either the tip section 14 or the distal region 40. In that regard, the tubing 39 has a flexibility durometer rating lesser than either the intermediate section 14 or the distal region 40 and ranging between about 35D to 60D, more preferably about 55D. The lesser flexibility of the tip section 14 and the distal region 40 relative to the proximal region 38 (due to the underlying tubing structure and/or internal structures or wires extending therethrough) enables the user to manipulate the mapping assembly 17 to reach the target site, and further to manipulate the circular segment 46 to enter into and releasably anchor itself in a tubular region, e.g., a pulmonary vein. With a greater flexibility, the proximal region 38 can then be manipulated to generally lie flat against wall tissue around an ostium of the tubular region, as shown in FIG. 5. In accordance with a feature of the present invention, the proximal region 38 has greater softness, floppiness and/or flexibility relative to the intermediate section 14 and the distal region 40 of the mapping assembly 17.

Figure 9:
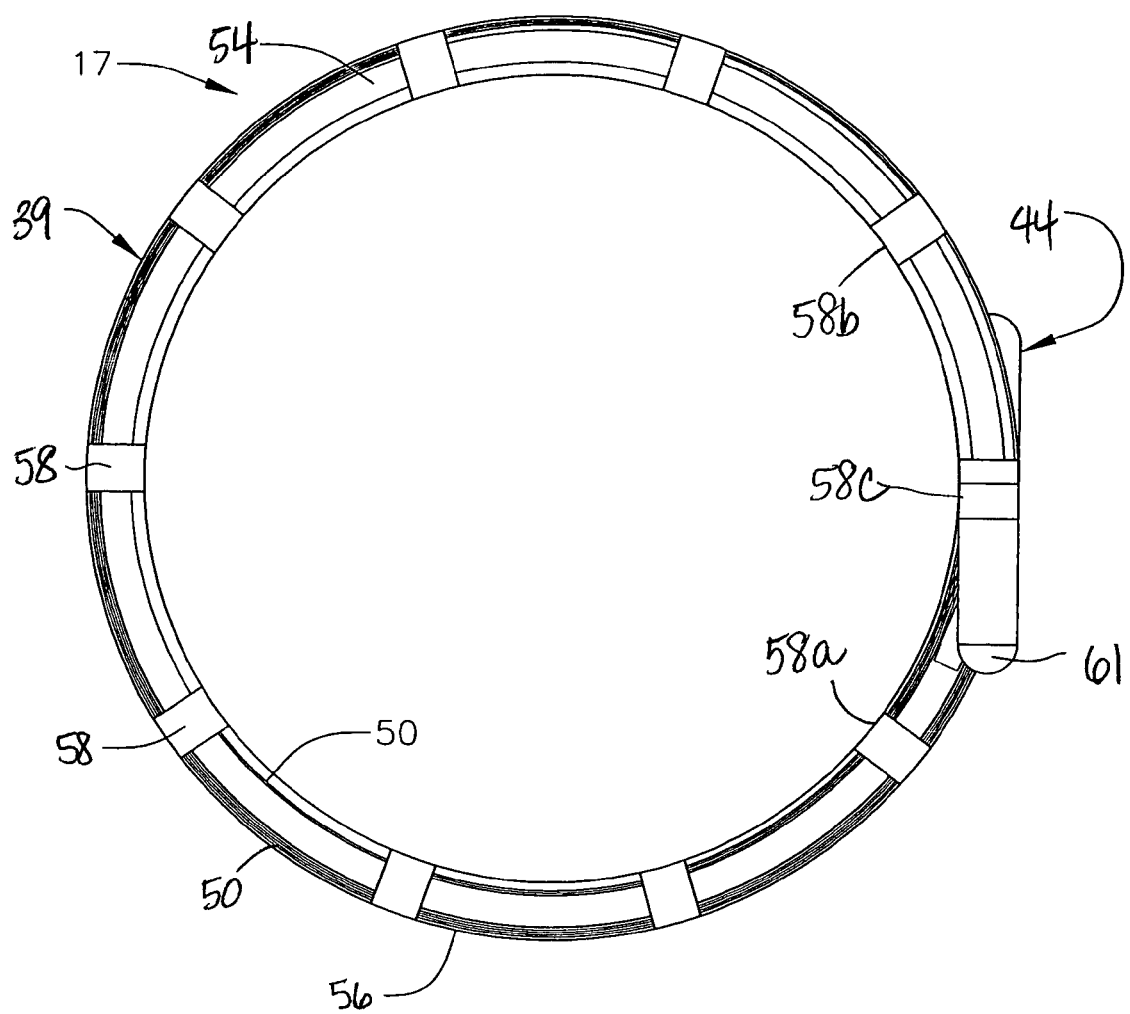
FIG. 9 is a schematic view of an embodiment of the mapping assembly according to the present invention.
Figure 10:
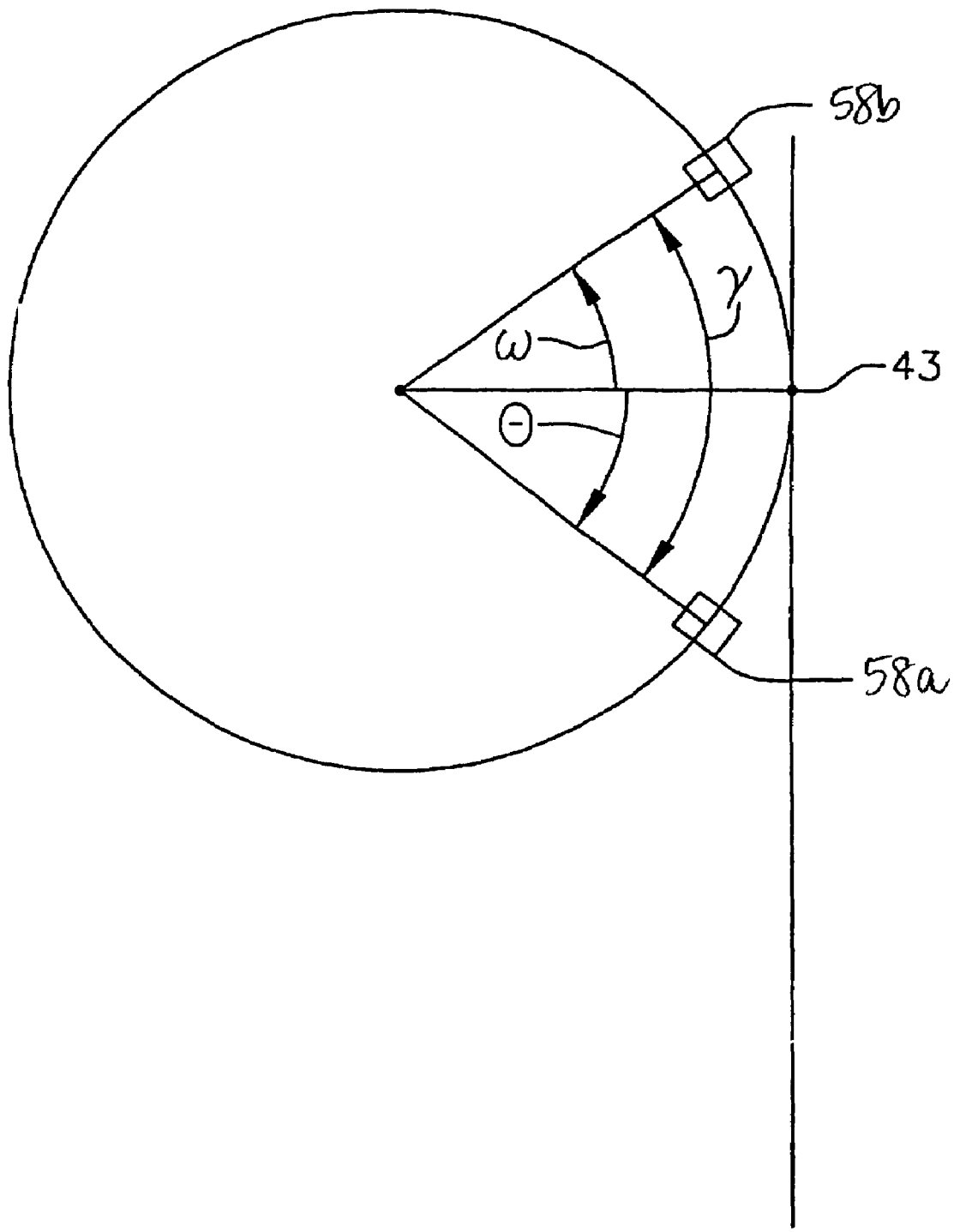
FIG. 10 is a schematic view of the mapping assembly according to the present invention depicting the relationship between two electrodes.
Figure 11:
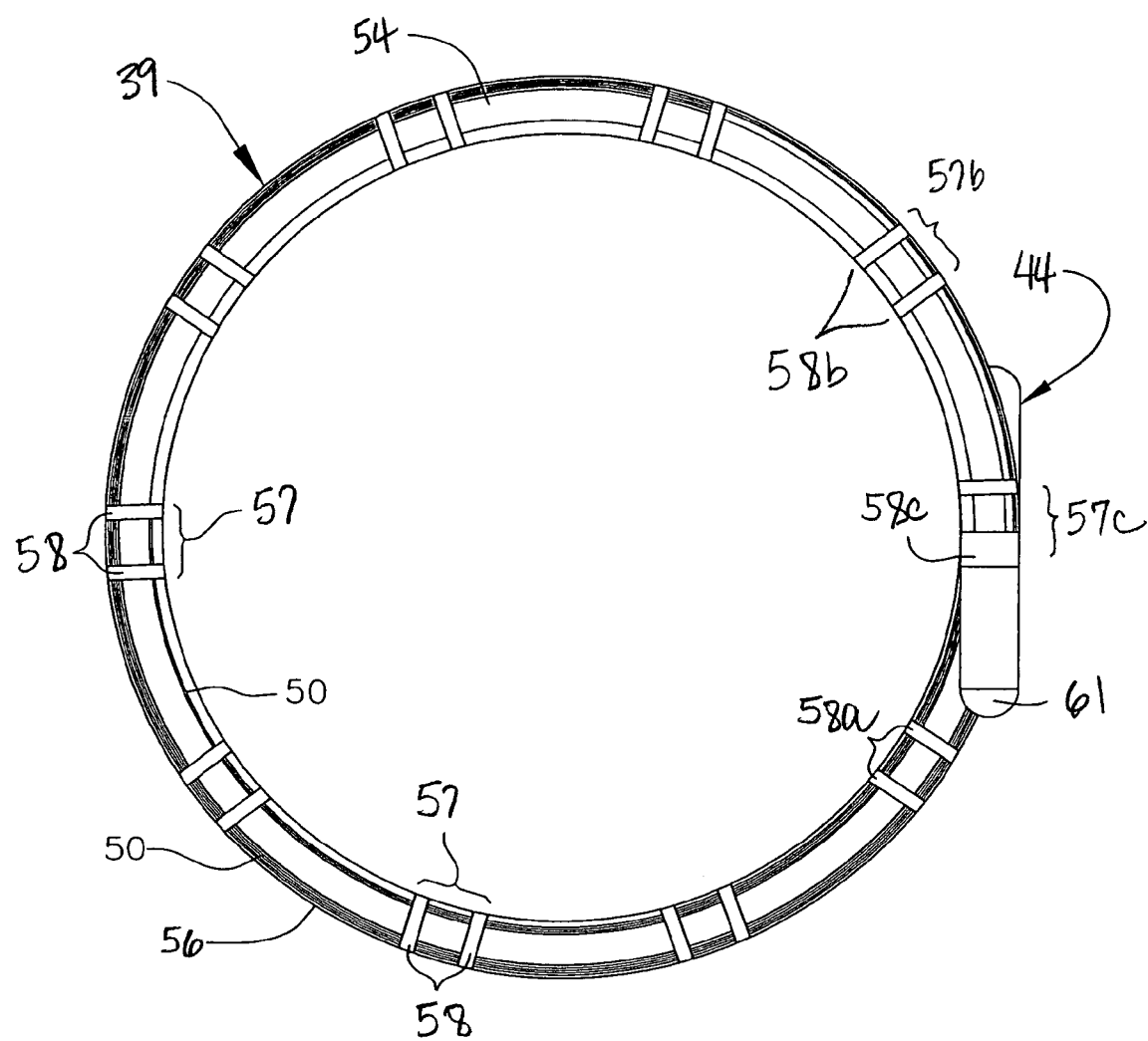
FIG. 11 is a schematic view of an alternative embodiment of the mapping assembly according to the present invention.

If desired, additional electrodes 58 could be mounted along the circular segment of the distal region distal region 40. FIG. 9 shows one electrode arrangement for the circular segment 39. As explained above, the generally circular main segment 39 is very slightly helical, although FIGS. 9 and 11 depict the main segment 39 as a flat circle, as it would generally appear when viewed from the distal end of the catheter. Referring to both FIGS. 9 and 10, a first ring electrode 58a is provided, which is the electrode that is on the generally circular main segment 46 closest to the transitional segment 44. A second electrode 58b is provided, which is the electrode that is on the generally circular main segment 46 adjacent its tangent location 43 (FIG. 10). Preferably, the first electrode 58a is positioned along the circumference of the generally circular main segment 46 at a distance .theta. of no more than about 55.degree. from the tangent location 43, more preferably no more than about 48.degree. from the tangent location, still more preferably from about 15.degree. to about 36.degree. from the tangent location. Preferably the second electrode 58b is positioned along the circumference of the generally circular main segment at a distance .omega. of no more than about 55.degree. degrees from the tangent location, more preferably no more than about 48.degree. from the tangent location 43, still more preferably from about 15.degree. to about 36.degree. from the tangent location. Preferably the first electrode 58a is positioned along the circumference of the generally circular segment at a distance .gamma. of no more than 100.degree. from the second electrode 58b, preferably no more than 80.degree. from the second electrode, still more preferably from about 30.degree. to about 75.degree. from the second electrode. There is also shown an electrode 58c in FIG. 9. which is longer than the other ring electrodes, preferably having a length ranging from about 1 mm to about 1.5 mm. The longer ring electrode provides a signal to the user when the catheter is being viewed under fluoroscopy. By having one ring electrode, such as the electrode 58c, sized differently from the other ring electrodes, the user has a reference point when viewing the catheter under fluoroscopy.

FIG. 11 shows another electrode arrangement for the main segment 46 where generally the single ring electrodes 58 have been configured into electrode pairs 57. It is understood that lead wires 50b for the electrodes 58 may extend parallel with the support member 58 through the nonconductive covering 58 of the distal region 40 and through the lumen of the tubing 39 of the proximal region 38, as shown in FIG. 6b.

As shown in the embodiment of FIGS. 1-11, the distal end of the generally circular segment 46 may be capped, preferably with polyurethane glue, to form an atraumatic cap 61 (FIGS. 4 and 5) and to prevent body fluids from entering the mapping assembly 17.

Figure 12:
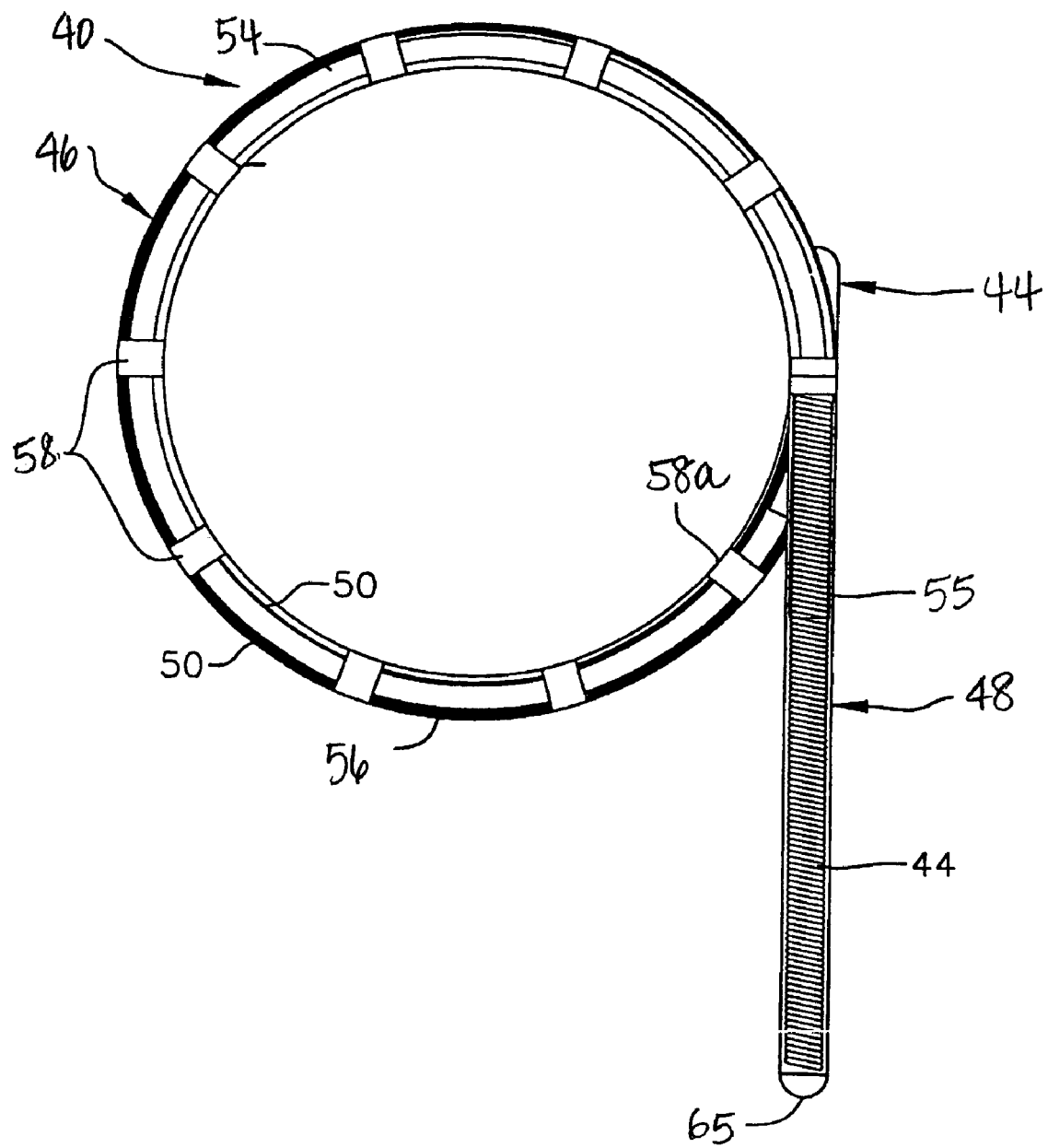
FIG. 12 is a schematic view of another alternative embodiment of the mapping assembly according to the present invention.
Figure 13:
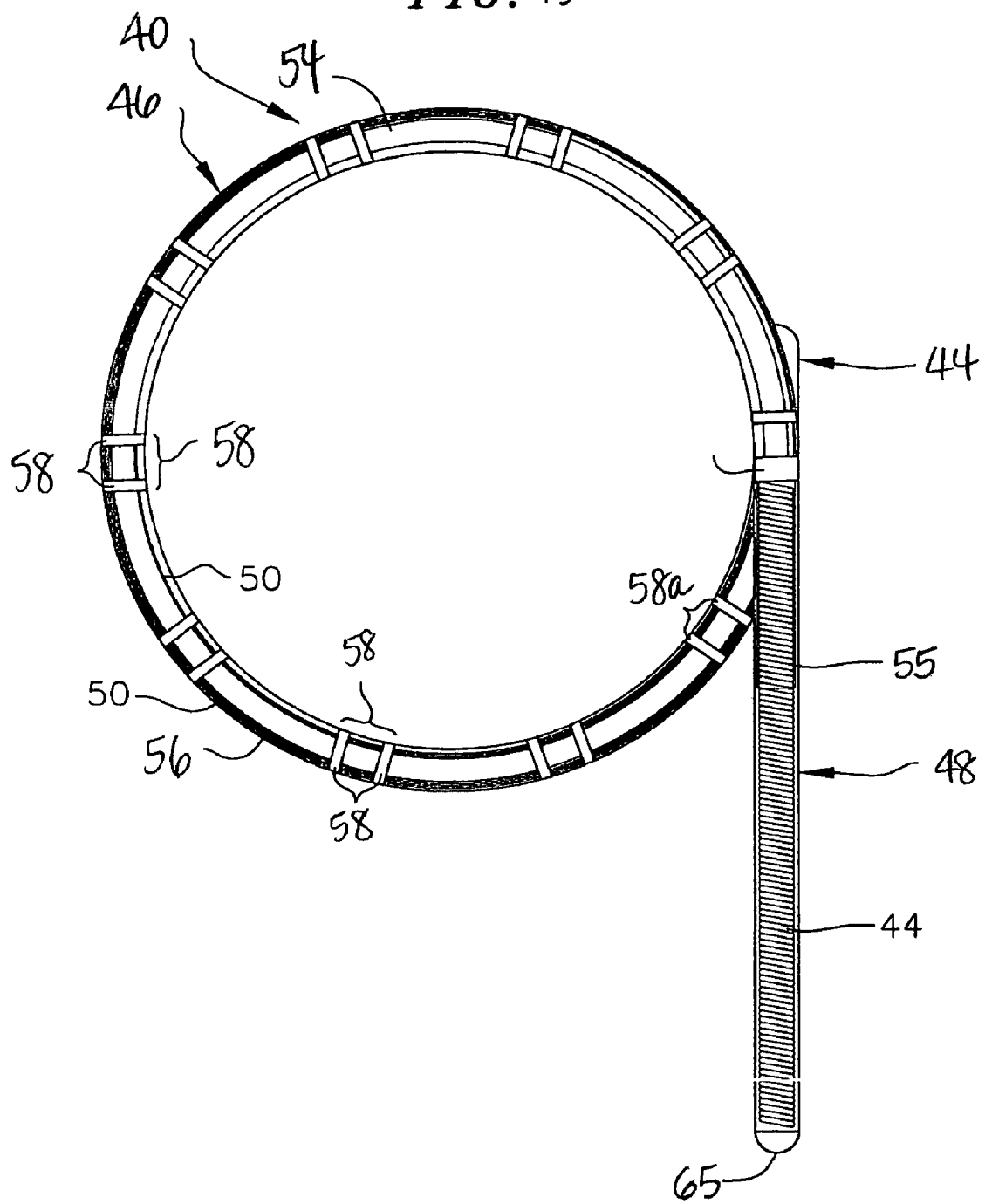
FIG. 13 is a schematic view of yet another alternative embodiment of the mapping assembly according to the present invention.
Figure 15:
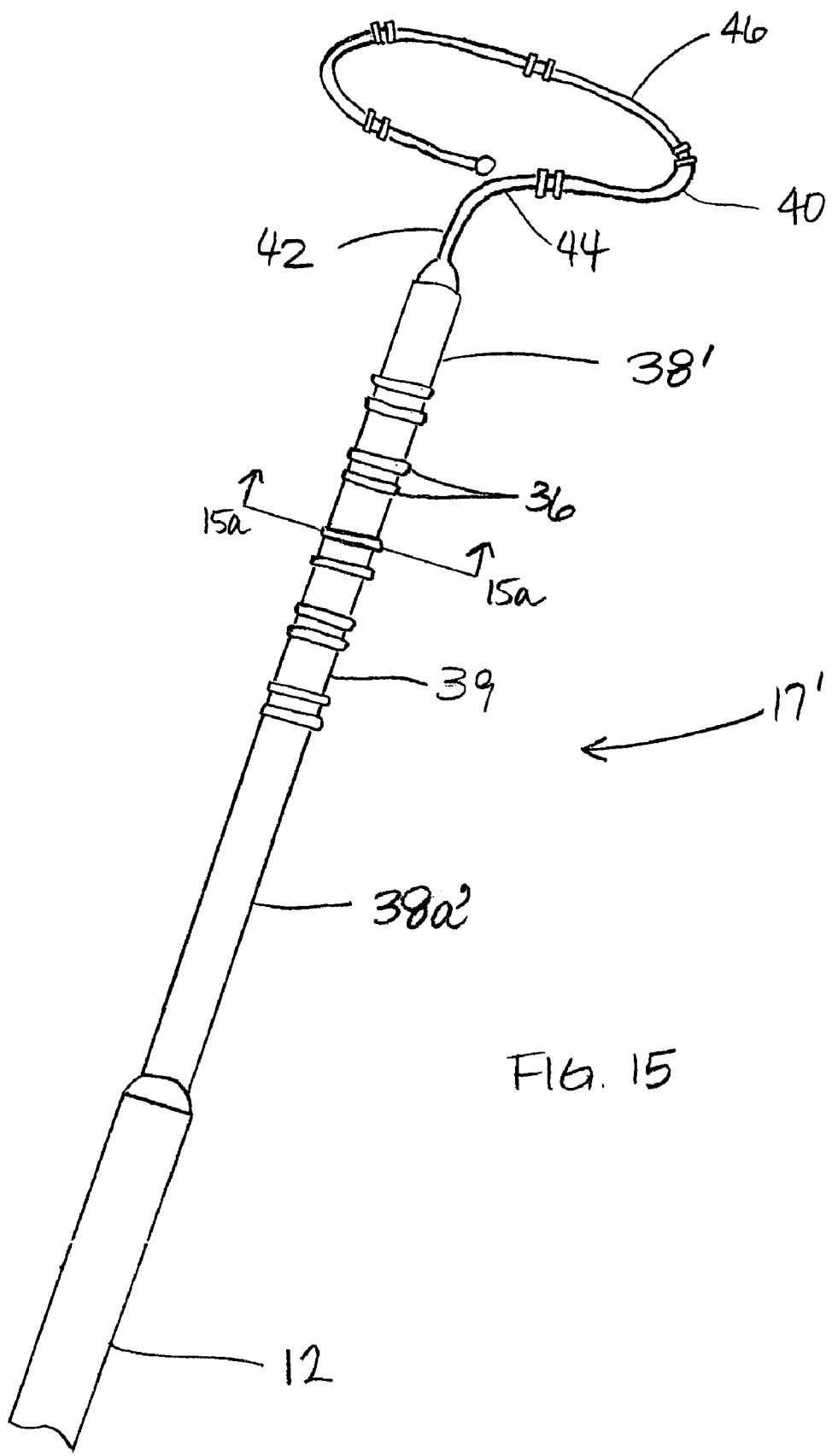
FIG. 15 is a schematic perspective view of an embodiment of the mapping assembly of FIG. 14.
Figure 16:
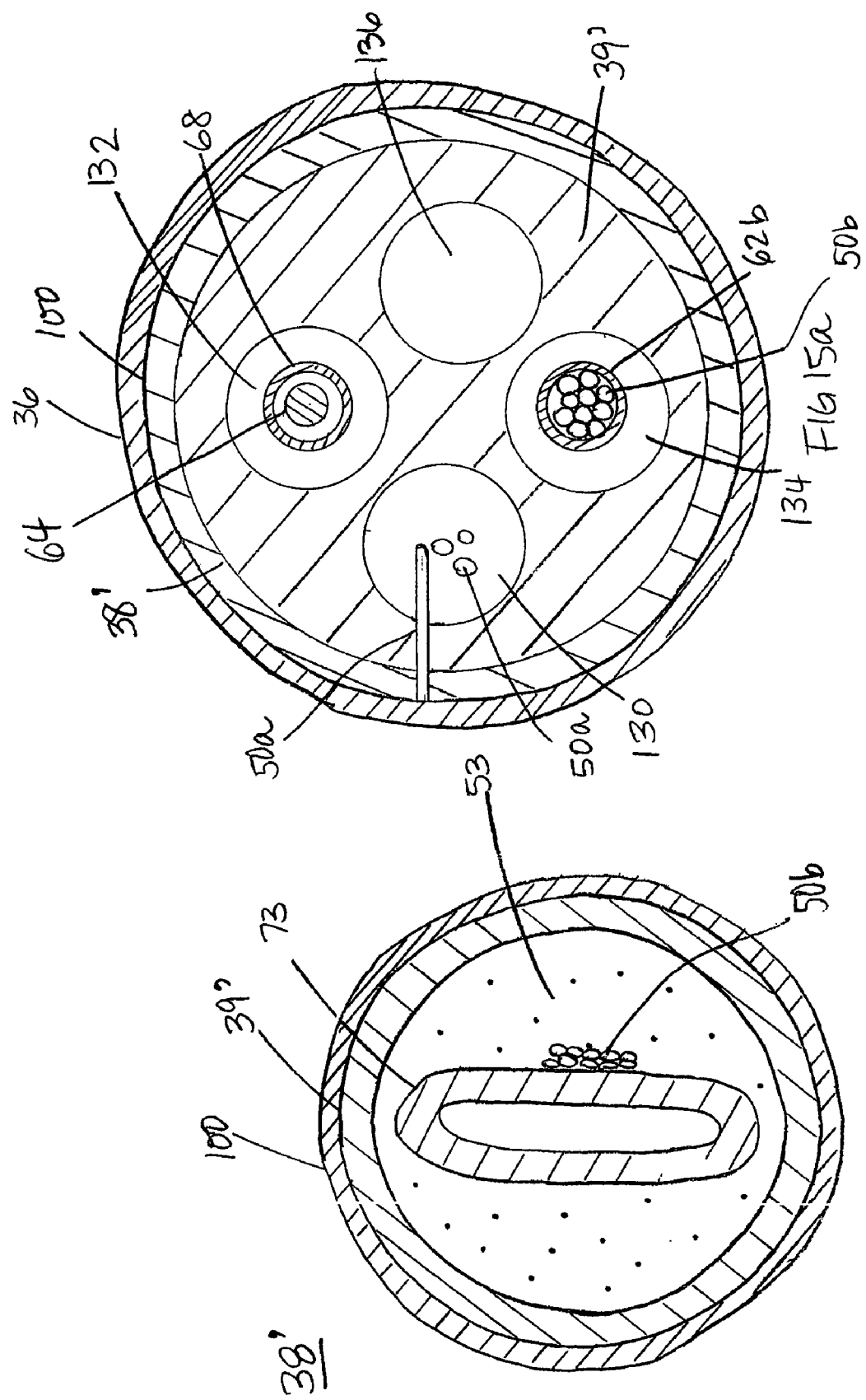
FIG. 16 is a side cross sectional view of the catheter body of FIG. 1, including the junction between the catheter body and the mapping assembly.
Figure 17:
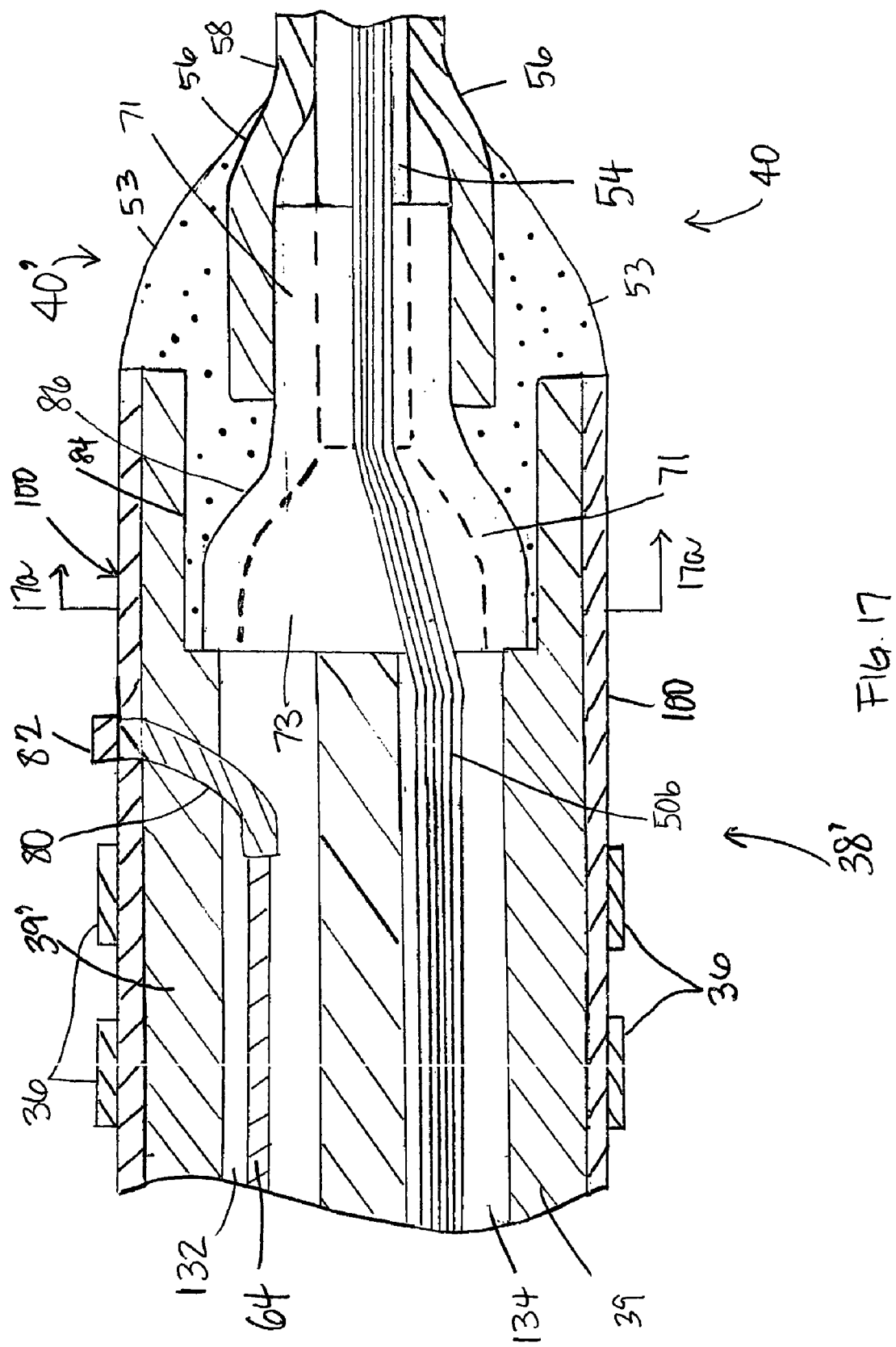
FIG. 17 is a side cross sectional view of an alternative embodiment of the junction between the proximal and distal regions of the mapping assembly, with lead wires for electrodes carried on the distal region.
Figure 17B:
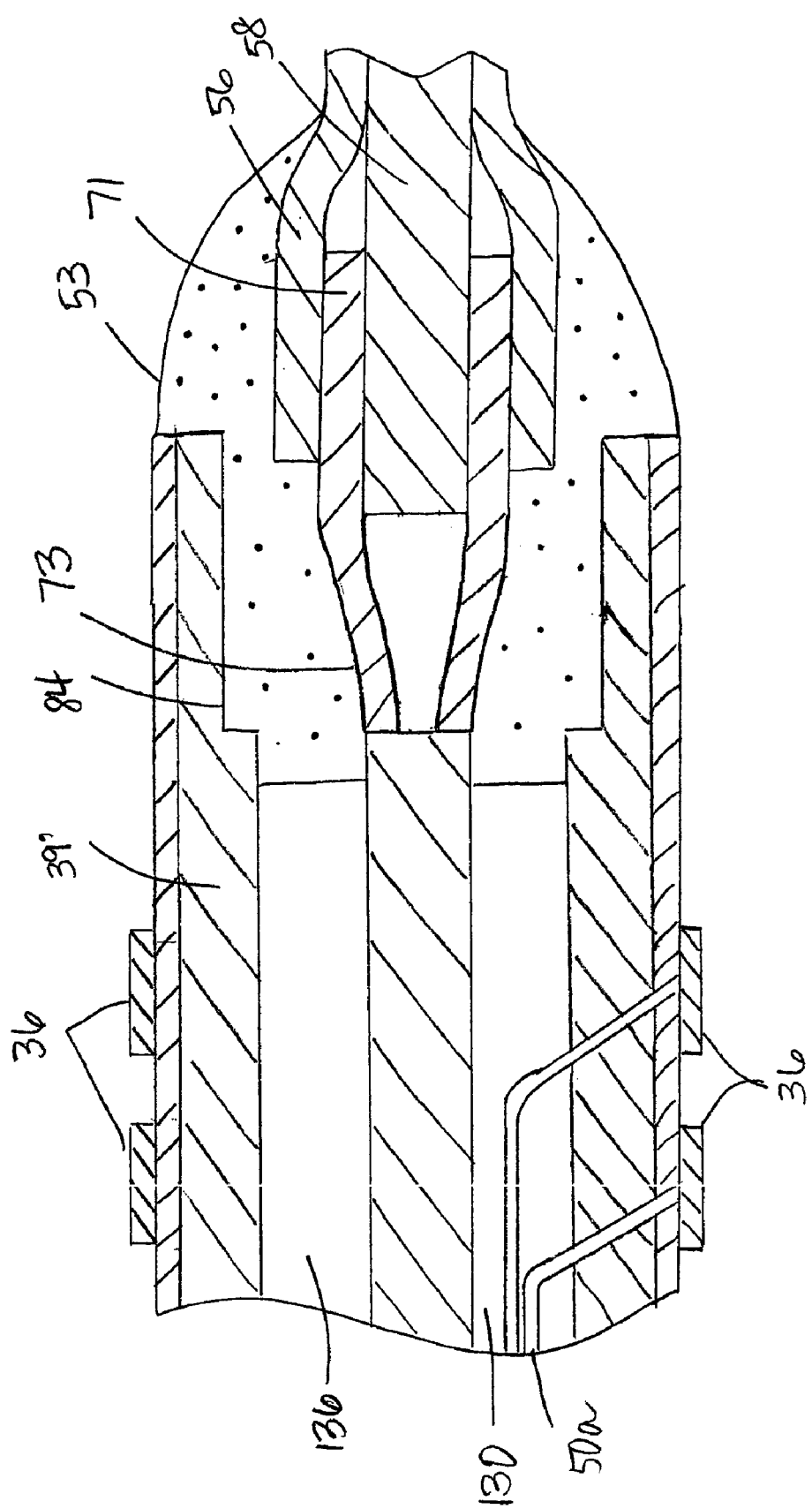
FIG. 17b is a side cross sectional view of an alternative embodiment of the junction between the proximal and distal regions of the mapping assembly.

In an alternative design as shown in FIGS. 12 and 13, the mapping assembly 17 includes a generally straight distal segment 48 which forms a tangent relative to the generally circular segment and contacts the main segment at the tangent location. The generally straight distal segment 48 is provided with an atraumatic design to prevent the distal end of the mapping assembly 17 from penetrating tissue. In the depicted embodiment, the distal segment comprises a tightly wound coil spring 44 made, for example, of stainless steel, such as the mini guidewire commercially available from Cordis Corporation (Miami, Fla.) or a coil having a 0.0045 inch wire size and a 0.009 inch inner diameter, such as that commercially available from Microspring. The coil spring 44 is mounted at its proximal end in a short piece of tubing 55 with polyurethane glue or the like, which is then glued or otherwise anchored within the non-conductive covering. The tubing 55 is less flexible than the nonconductive covering 56 but more flexible than that support member 54 to provide a transition in flexibility along the length of the mapping assembly 17. The distal end of the distal segment 40 is capped, preferably with polyurethane glue 65, to prevent body fluids from entering the mapping assembly 17.

In the depicted embodiment, the generally straight distal segment 48 has a length of about 0.5 inch, but can be any desired length, for example, ranging from about 0.25 inch to about 1.0 inch. The generally straight distal segment 48 is preferably sufficiently long to serve as an anchor for introducing the catheter into a guiding sheath, as discussed in more detail below, because the mapping assembly 17 must be straightened upon introduction into the sheath. Without having the generally straight distal segment 48 as an anchor, the mapping assembly 17 has a tendency to pull out of the guiding sheath upon its introduction into the guiding sheath. Any other atraumatic tip design that prevents the distal end of the mapping assembly from penetrating tissue could be provided. An alternative design in the form of a plastic ball is described in copending patent application Ser. No. 09/370,605, entitled "ATRIAL BRANDING IRON CATHETER AND METHOD FOR TREATING ATRIAL FIBRILLATION", the entire disclosure of which is incorporated herein by reference. Additionally, if desired, the distal segment 48 can be formed, at least in part, of a radiopaque material to aid in the positioning of the mapping assembly 17 under fluoroscopy. A suitable and similar distal segment is disclosed in U.S. Pat. No. 6,711,428, the entire disclosure of which is incorporated by reference.

The lead wires 50 attached to the ring electrodes 36 extend through the lumen of the tubing 39 of the proximal region 38 (FIG. 6), through the first lumen 30 of the intermediate section 14 (FIG. 3), through the central lumen 18 of the catheter body 12 (FIG. 2), and the control handle 16, and terminate at their proximal end in the connector 37 (FIG. 1). The portion of the lead wires 50 extending through the central lumen 18 of the catheter body 12, control handle 16 and proximal end of the intermediate section 14 are enclosed within a protective sheath 62 (FIG. 2), which can be made of any suitable material, preferably polyimide. The protective sheath 62 is anchored at its distal end to the proximal end of the intermediate section 14 by gluing it in the first lumen 30 with polyurethane glue or the like.

The puller wire 64 is provided for deflection of the intermediate section 14. The puller wire 64 extends through the catheter body 12 (FIG. 2) and the second lumen 32 of the intermediate section 14 (FIG. 3). The puller wire 64 is anchored at its proximal end to the control handle 16, and is anchored at its distal end to the intermediate section 14. The puller wire 64 is made of any suitable metal, such as stainless steel or Nitinol, and is preferably coated with Teflon™. or the like. The coating imparts lubricity to the puller wire 64. The puller wire 64 preferably has a diameter ranging from about 0.006 to about 0.010 inch.

As shown in FIG. 2, a compression coil 66 is situated within the catheter body 12 in surrounding relation to the puller wire 64. The compression coil 66 extends from the proximal end of the catheter body 12 to the proximal end of the intermediate section 14. The compression coil 66 is made of any suitable metal, preferably stainless steel. The compression coil 66 is tightly wound on itself to provide flexibility, i.e., bending, but to resist compression. The inner diameter of the compression coil 66 is preferably slightly larger than the diameter of the puller wire 64. The Teflon.RTM. coating on the puller wire 64 allows it to slide freely within the compression coil 66. The outer surface of the compression coil 66 is covered by a flexible, non-conductive sheath 68, e.g., made of polyimide tubing.

The compression coil 66 is anchored at its proximal end to the outer wall 20 of the catheter body 12 by proximal glue joint 70 and at its distal end to the intermediate section 14 by distal glue joint 72. Both glue joints 70 and 72 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 20 of the catheter body 12 which is heated sufficiently to form a permanent hole. The glue is then introduced through the hole to the outer surface of the compression coil 66 and wicks around the outer circumference to form a glue joint about the entire circumference of the compression coil.

In use, a suitable guiding sheath is inserted into the patient with its distal end positioned at a desired mapping location, for example, the left atrium of the heart. An example of suitable guiding sheath for use in connection with the present invention is the Preface.™. Braiding Guiding Sheath, commercially available from Cordis Webster (Diamond Bar, Calif.). The distal end of the sheath is guided into one of the atria. A catheter in accordance with the present invention is fed through the guiding sheath until its distal end extends out of the distal end of the guiding sheath. As the catheter id fed through the guiding sheath, the mapping assembly 17 is straightened to fit through the sheath. Once the distal end of the catheter is positioned at the desired mapping location, the guiding sheath is pulled proximally, allowing the deflectable intermediate section 14 and mapping assembly 17 to extend outside the sheath, and the distal region 40 of the mapping assembly 17 returns to its original shape due to the shape-memory of the support member 54. The distal region 40 of the mapping assembly 17, in particular, the generally circular main segment 46 (with or without the distal segment 48) is then inserted into a pulmonary vein 70 (FIG. 5) so that the outer circumference of the generally circular main segment 46 of the assembly is in contact with a circumference inside the tubular region. Preferably at least about 50%, more preferably at least about 70%, and still more preferably at least about 80% of the circumference of the generally circular main segment 46 is in contact with a circumference inside the tubular region. As such, the circular segment 46 is therefore releasably anchored in the tubular region, e.g., a pulmonary vein 70 which enables the more flexible proximal region 38 carrying the electrodes 36 to contact and lay flat against wall tissue near and surrounding an ostium 72 or extending between the ostium 72 and another ostium 74 of another pulmonary vein. Consequently, a user can bridge the linear gap between pulmonary veins for mapping and/or ablation purposes with one placement of the catheter instead of multiple placements. Benefits thereof include the ability to guide burns to locations that do not show yet a complete lesion and the ability to obtain a complete linear lesion with fewer burns. In particular, the configuration including the length of the proximal region 38 enables the proximal region 38 to serve as a generally linear template or guide against which another catheter tip can be moved along.

The releasable anchoring and stabilization provided by the circular segment 46 generally enables the distal region 40 to remain relatively stationary in the tubular region while the proximal region 38 can be manipulated to rotate about the ostium 72 so as to sweep a circular region around the ostium 72. For example, if an angle zero is defined by an axis extending between the ostia 72 and 74, the proximal region 38 may be manipulated to sweep out 360 degrees around the ostium 72. With the generally linear mapping configuration of the electrodes 36 carried on the proximal region 38, a multitude of radially extending linear mappings can be accomplished about the ostium 72 as the proximal region 38 is rotated about the ostium 72. Moreover, when such linear mappings are completed, the circular segment 46 can be inserted into the ostium 74 where a multitude of radially extending linear mappings can be accomplished about the ostium 74.

Where the circular segment 46 carries the electrodes 58, the circular arrangement of the electrodes 58 permits measurement of the electrical activity at that circumference of the tubular structure so that ectopic beats between the electrodes 58 can be identified. The size of the generally circular main segment 46 permits measurement of electrical activity along a diameter of a pulmonary vein or other tubular structure of or near the heart because the circular main segment has a diameter generally corresponding to that of a pulmonary vein or the coronary sinus. Additionally, because the main segment 46 need not form a flat circle, but can be somewhat helical, it is easier for the user to guide the mapping assembly 17 into a tubular region.

In an alternative embodiment of the present invention, the catheter 10 of FIGS. 14-17, where similar components are designated by similar reference numerals, generally except as discussed herein, the distal end of the catheter body 12 is joined with the proximal end of a mapping assembly 17' having a proximal region 38' and a distal region 40. The useful length of the catheter may range between about 110 cm and about 120 cm, and more preferably about 115 cm.

In the illustrated embodiment, the proximal region 38' is more flexible than either the catheter 12 and the mapping assembly 17' and includes an elongated proximal segment 38a' that is generally devoid of electrodes serving generally the same function as describe hereinabove in relation to the segment 38a. The proximal region 38' comprises a tubing 39' having a length ranging between about 60 mm and about 70 mm and preferably about 65 mm having at least three lumens 130, 132 and 134, which may or may not of equal size but may be about 0.025 inches in diameter. There may also be a fourth lumen 136 which may be occupied by other wires or tubing. In one embodiment, the tubing 39' comprises pellathane and barium sulfate. In particular, the tubing 39' comprises pellathane of two different durometer rating and barium sulfate. In a particularly preferred embodiment, the tubing 39' comprises about 53% pellathane of about 55D durometer, about 10% pellathane of 80A durometer (where A is a lower level hardness scale than D, which defines 80A as softer than 55D), about 36% barium sulfate and about 1% color and other components for use in the extrusion of the tubing 39'. It is understood that the barium sulfate is used for radio-opacity. In general, the proximal region 38' is less flexible than the aforementioned proximal region 38 in the first embodiment. Surrounding the tubing 39' may be a stainless steel braid tubing 100 for increasing torque and stiffness in the tubing 39'.

Extending through the lumen 130 of the tubing 39' are lead wires 50a for the ring electrodes 36 on the proximal region 38'. The ring electrode pairs on the proximal region 38' are generally spaced apart a distance of about 5 mm, with each electrode within a pair separated by a distance of about 1.0 mm. Extending through the lumen 132 is the puller wire 64 whose distal end is anchored to the distal end of the proximal tubing 39' by means of the tubular stainless steel 80 and cross-piece 82. Accordingly, in this embodiment, it is understood that the puller wire 64 enables the catheter to deflect generally along the length of the proximal region 38'. Extending through the lumen 134 are lead wires 50b for the electrodes 57 on the generally circular segment 46 of the distal region 40. The lead wires 50b extend alongside the support member 54 and the spade 73 and inside the covering 56 and then through the lumen 134 of the tubing 39. The lead wires then may extend further proximally through a nonconductive sheath 62b whose distal end terminates at the proximal end of the tubing 39. Any other additional wires (such as a contraction wire for the segment 46), or tubing (such as an irrigation tubing) may extend through the lumen 136.

It is understood by one of ordinary skill in the art that the distal region 40 may assume other embodiments and configurations. For example, other suitable anchoring mechanisms may include balloons, deflectable tips, expanding mechanisms or needle-type anchoring mechanisms. There may be a pre-curve set in the distal portion of the catheter to allow the floppy proximal region 38 to flop in a desired plane. In that regard, a passive bend shape is added to the catheter by cooking it at high temperature(but below melting temperature) while bent in the desire shape. It allows for easier catheter placement in specific anatomy, if the pre-curve is optimized for that anatomy, and it also makes the catheter predisposed to bending in a particular manner during active deflection.

If desired, two or more puller wires can be provided to enhance the ability to manipulate the intermediate section 14. In such an embodiment, a second puller wire and a surrounding second compression coil extend through the catheter body and into an additional off-axis lumen in the intermediate section. The first puller wire is preferably anchored proximal to the anchor location of the second puller wire. Suitable designs of catheters having two or more puller wires, including suitable control handles for such embodiments, are described, for example, in U.S. patent application Ser. No. 08/924,611, filed Sep. 5, 1997; Ser. No. 09/130,359; filed Aug. 7, 1998; Ser. No. 09/143,426, filed Aug. 28, 1998; and Ser. No. 09/157,055, filed Sep. 18, 1998, the disclosures of which are incorporated herein by reference.

Moreover, the control handle can be configured with a contraction wire to manipulate a contraction of the circular segment 46. The support member 54 is pre-shaped with a curvature ranging between about 340 degrees and 380 degrees, and more preferably about 360 degrees, between the proximal end of the circular segment 46 (at the junction with the distal end of the transition segment 44) and the distal end of the circular segment 46. With manipulation of the contraction wire, the diameter of the circular segment is contracted to increase the degree of curvature. The distal end of the circular segment 46 is drawn toward the proximal end by the contraction wire whose distal end is attached to the distal end of the circular segment 46 and whose proximal end is in the control handle. A suitable contraction wire and controlling mechanism are disclosed in pending application U.S. Ser. Nos. 10/386,872 and 10/386,594, the entire disclosures of which are incorporated herein.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention and that the drawings may not be to scale.

Accordingly, the foregoing description should not be read as pertaining only to the precise structures described and illustrated in the accompanying drawings, but rather should be read consistent with and as support to the following claims which are to have their fullest and fair scope.

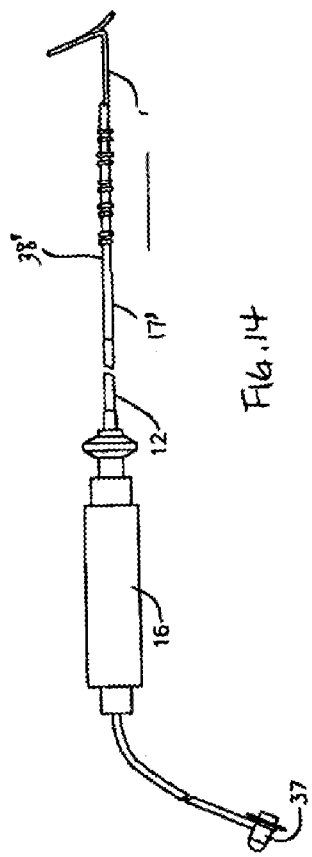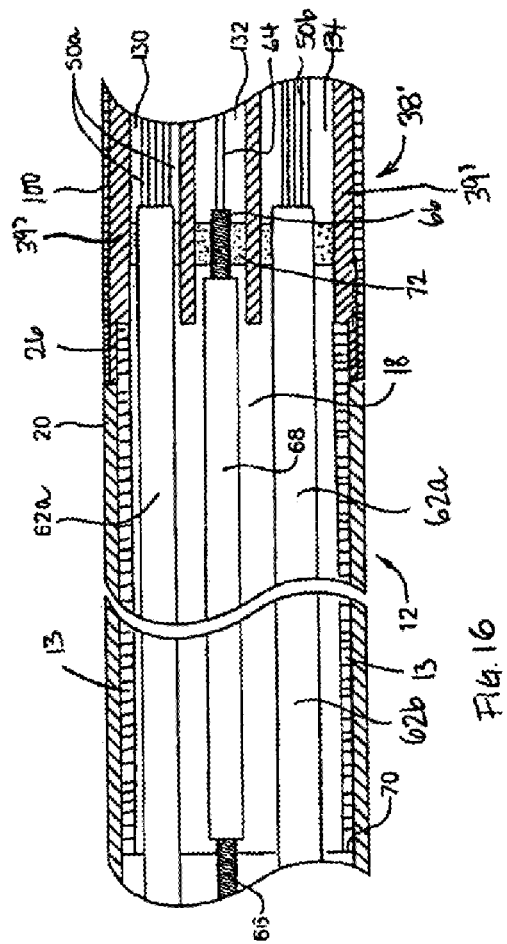

What is claimed is:

1. A mapping catheter adapted for mapping near a tubular region of a heart, comprising:
    an elongated tubular catheter body having an outer wall, proximal and distal ends, and at least one lumen extending therethrough;
    an intermediate section having proximal and distal ends, the intermediate section being distal of the catheter body; and
    a mapping assembly at the distal end of the intermediate section, the mapping assembly having:
        a generally circular main segment with a support member having shape-memory disposed within at least the main segment of the mapping assembly,
        a generally linear segment proximal the generally circular main segment, the generally linear segment having greater flexibility than either of the intermediate section and the generally circular main segment, and a plurality of ring electrodes on the generally linear segment, wherein the generally circular main segment is adapted to releasably anchor itself in the tubular region and wherein the generally linear segment is adapted to contact generally along its length heart wall tissue near an ostium of the tubular region.

2. A catheter according to claim 1, further comprising a second plurality of electrodes on the generally circular main segment.

3. A catheter according to claim 1, wherein the proximal segment carrying the electrodes is adapted to conduct mapping of said wall tissue along a linear pattern extending radially from the ostium.

4. A catheter of claim 3, wherein the mapping assembly is adapted to be rotated about the ostium to perform mapping of said wall tissue along different radially-extending linear patterns about the ostium.

5. A catheter of claim 1, wherein the support member is nitinol.

6. A catheter of claim 1, wherein the generally linear segment comprises a tubing with flexibility durometer rating of about 55 D.

7. A catheter of claim 1, wherein the generally linear segment has an exposed length ranging between about 30 mm to 70 mm.

8. A catheter of claim 1, wherein the generally linear segment has an exposed length of about 30 mm.

9. A catheter of claim 1, further comprising a first puller wire to manipulate deflection of the intermediate section.

10. A catheter of claim 1, wherein the mapping assembly further comprises a generally straight distal segment distal of the generally circular segment.

11. A catheter of claim 1, wherein the generally circular main segment has an outer diameter ranging to about 10 mm to about 35 mm.

12. A catheter of claim 1, wherein the generally circular main region has an outer diameter ranging between about 12 mm to about 20 mm.

13. A catheter of claim 1, wherein the plurality of ring electrodes comprises a plurality of ring electrode pairs, wherein a number of ring electrode pairs along the generally linear proximal segment ranges from about two to about twenty.

14. A catheter of claim 1, comprising ten ring electrode pairs along the generally linear segment.

15. A catheter of claim 1, further comprising additional ring electrodes carried on the generally circular segment.

16. A catheter according to claim 1, further comprising means for deflecting the intermediate section without altering the shape of the mapping assembly.

17. A catheter according to claim 16, wherein the deflecting means comprises:

a puller wire extending through a lumen of the catheter body, said puller wire being fixedly attached at its distal end to the intermediate section near the distal end of the intermediate section; and a control handle for moving the puller wire longitudinally relative to the catheter body to thereby cause deflection of at least the intermediate section.

18. A catheter of claim 1, wherein the generally linear segment of the mapping assembly comprises an elongated proximal segment that is generally devoid of electrodes and adapted to define an angle with the intermediate section ranging between about 45 degrees to about 315 degrees.

19. A method for mapping electrical activity of wall tissue near a tubular region of or near the heart, the method comprising:

inserting the generally circular segment of a catheter according to claim 1 into a tubular region of or near the heart;

releasably anchoring the generally circular segment in the tubular region near its ostium;

contacting the generally linear segment of the catheter generally along its length with wall tissue near the ostium; and mapping the electrical activity of the wall tissue along a linear pattern extending radially from the ostium.

20. A method of claim 19, further comprising:

rotating the mapping assembly about the ostium and mapping the electrical activity of the wall tissue along a different linear pattern extending radially from the ostium.

21. A method according to claim 19, wherein the tubular region is selected from the group consisting of pulmonary veins, the coronary sinus, the superior vena cava, and the inferior vena cava.

22. A method according to claim 19, wherein the tubular region is a pulmonary vein.

23. A mapping catheter adapted for mapping near a tubular region of a heart, comprising:

an elongated tubular catheter body having an outer wall, proximal and distal ends, and at least one lumen extending therethrough;

an intermediate section having proximal and distal ends, the intermediate section being distal of the catheter body; and a mapping assembly at the distal end of the intermediate section, the mapping assembly having a distal portion and a generally linear segment proximal the distal portion, the generally linear segment having greater flexibility than either of the intermediate section and the distal portion, and a plurality of ring electrodes carried on the generally linear segment, wherein the distal portion is adapted to releasably anchor itself in the tubular region and wherein the generally linear segment is adapted to contact generally along its length heart wall tissue near an ostium of the tubular region.

24. A catheter according to claim 23, wherein the proximal segment carrying the electrodes is adapted to conduct mapping of said wall tissue along a linear pattern extending radially from the ostium.

25. A catheter of claim 24, wherein the mapping assembly is adapted to be rotated about the ostium to perform mapping of said wall tissue along different radially-extending linear patterns about the ostium.

26. A catheter of claim 23, wherein the generally linear segment comprises a tubing with flexibility durometer rating of about 55 D.

27. A catheter of claim 23, wherein the generally linear segment has an exposed length ranging between about 30 mm to 70 mm.

28. A catheter of claim 23, wherein the generally linear segment has an exposed length of about 42 mm.

29. A catheter of claim 23, further comprising a first puller wire to manipulate deflection of the intermediate section.

30. A mapping catheter adapted for mapping near a tubular region of a heart, comprising:

an elongated tubular catheter body having an outer wall, proximal and distal ends, and at least one lumen extending therethrough;

a mapping assembly distal of the distal end of the catheter body, the mapping assembly having:
- a generally circular main segment with a support member having shape-memory disposed within at least the main segment of the mapping assembly,
- a generally linear segment proximal the generally circular main segment, the generally linear segment having greater flexibility than both the catheter body and the generally circular main segment, and
- a plurality of ring electrodes on the generally linear segment, wherein the generally circular main segment is adapted to releasably anchor itself in the tubular region and wherein the generally linear segment is adapted to contact generally along its length heart wall tissue near an ostium of the tubular region.

31. A catheter according to claim 30, further comprising a second plurality of electrodes on the generally circular main segment.

32. A catheter according to claim 30, wherein the generally linear segment carrying the electrodes is adapted to conduct mapping of said wall tissue along a linear pattern extending radially from the ostium.

33. A catheter of claim 32, wherein the linear segment is adapted to guide a second catheter to move along said linear pattern.

34. A catheter of claim 30, wherein the mapping assembly is adapted to be rotated about the ostium to perform mapping of said wall tissue along different radially-extending linear patterns about the ostium.

35. A catheter of claim 34, wherein the linear segment is adapted to guide a second catheter to move along said linear patterns.

36. A catheter of claim 30, further comprising a puller wire to manipulate deflection of an intermediate section between the catheter body and the mapping assembly.

37. A catheter of claim 30, further comprising a puller to manipulate deflection of the linear segment of the mapping assembly.

* * * * *

UNITED STATES PATENT AND TRADEMARK OFFICE
CERTIFICATE OF CORRECTION

PATENT NO.        : 7,412,273 B2
APPLICATION NO.   : 10/990146
DATED             : August 12, 2008
INVENTOR(S)       : Pierre Jais It is certified that error appears in the above-identified patent and that said Letters Patent is hereby corrected as shown below:

In the Drawings

| | |
|---|---|
| Fig. 14, Sheet 14 of 18 | Delete Drawing Sheet 14 and substitute therefore the Drawing Sheet, consisting of Fig. 14, as shown on the attached page (Delete wording "Fig. 18") |
| Column 13, line 24, Claim 6 | Delete "with flexibility", Insert --with a flexibility-- |
| Column 14, line 54, Claim 26 | Delete "with flexibility", Insert --with a flexibility-- |

Signed and Sealed this

Tenth Day of February, 2009

JOHN DOLL
*Acting Director of the United States Patent and Trademark Office*